United States Patent [19]
Pieper

[11] Patent Number: 6,151,404
[45] Date of Patent: *Nov. 21, 2000

[54] ANATOMICAL VISUALIZATION SYSTEM

[75] Inventor: Steven D. Pieper, Thetford Center, Vt.

[73] Assignee: Medical Media Systems, West Lebanon, N.H.

[ * ] Notice: This patent issued on a continued prosecution application filed under 37 CFR 1.53(d), and is subject to the twenty year patent term provisions of 35 U.S.C. 154(a)(2).

[21] Appl. No.: 09/084,637

[22] Filed: May 26, 1998

Related U.S. Application Data

[63] Continuation of application No. 08/489,061, Jun. 9, 1995, abandoned, which is a continuation-in-part of application No. 08/457,692, Jun. 1, 1995, Pat. No. 5,737,506.

[51] Int. Cl.$^7$ ..................................................... G06K 9/00

[52] U.S. Cl. ........................... 382/128; 382/154; 434/267; 600/456

[58] Field of Search ........................... 250/363.04; 378/4, 378/21–27, 90; 382/128–134; 600/425, 437, 443, 456; 434/267

[56] References Cited

U.S. PATENT DOCUMENTS

| | | | |
|---|---|---|---|
| 4,722,056 | 1/1988 | Roberts et al. | 364/413 |
| 4,729,098 | 3/1988 | Cline et al. | 364/414 |
| 4,882,679 | 11/1989 | Tuy et al. | 364/413.22 |
| 4,922,909 | 5/1990 | Little et al. | 128/630 |

(List continued on next page.)

OTHER PUBLICATIONS

Kawata et al., Three–Dimensional Imaging of Blood Vessels Using Cone–Beam CT, Proceedings ICIP–94, IEEE Comput. Soc. Press, p. 140–144, Nov. 1994.

Klein et al., Identifying Vascular Features with Orientation Specific Filters and B–Spline Snakes, Computers in Cardiology 1994, IEEE Comput. Soc. Press, Sep. 1994.

Chen et al., "Left Ventricle Global Motion And Shape From CT Volumetric Data", IEEE Apr. 1993, pp. V–101 to V–104 (reprint).

VanRoden, "Don't Look Now, But a Body has Been Found in the Basement of Cummings Hall", Dartmouth Thayer School of Engineering Directions, a periodical published by the Trustees of Dartmouth College, Hanover, New Hampshire, vol. 8, No. 1, Fall 1993, pp. 30–36.

Roberts et al., "A frameless stereotaxic integration of computerized tomographic imaging and the operating microscope", J. Neurosurg./Vo. 65/Oct., 1986, pp. 545–549.

(List continued on next page.)

*Primary Examiner*—Jon Chang
*Assistant Examiner*—Jayanti K. Patel
*Attorney, Agent, or Firm*—Pandiscio & Pandiscio

[57] ABSTRACT

An anatomical visualization system is provided which includes a first database comprising a plurality of 2-D slice images generated by scanning a structure. The 2D slice images are stored in a first data format. A second database comprising a 3-D computer model of the scanned structure is also provided. The 3-D computer model includes a first software object defined by a 3-D geometry database. Apparatus is provided for inserting a second software object into the 3-D computer model so as to augment the 3-D computer model. The second software object is defined by a 3-D geometry database, and includes a planar surface. Apparatus for determining the specific 2-D slice image associated with the position of the planar surface of the second software object within the augmented 3-D computer model are provided in a preferred embodiment. Also provided are apparatus for texture mapping the specific 2-D slice image onto the planar surface of the second software object. Display apparatus is provided for displaying an image of the augmented 3-D computer model so as to simultaneously provide a view of the first software object and the specific 2-D slice image texture mapped onto the planar surface of the second software object. In another form of the invention, apparatus and method are provided for determining patient-specific anatomical dimensions using appropriate scanned 2-D slice image information.

6 Claims, 24 Drawing Sheets

U.S. PATENT DOCUMENTS

| | | | |
|---|---|---|---|
| 4,945,478 | 7/1990 | Merickel et al. | 364/413.22 |
| 4,965,844 | 10/1990 | Oka et al. | 382/44 |
| 4,985,855 | 1/1991 | Aldrich et al. | 364/522 |
| 4,989,083 | 1/1991 | Eino | 358/107 |
| 5,005,559 | 4/1991 | Blanco et al. | 128/4 |
| 5,151,856 | 9/1992 | Halmann et al. | 364/413.03 |
| 5,153,721 | 10/1992 | Eino et al. | 358/107 |
| 5,179,638 | 1/1993 | Dawson et al. | 395/125 |
| 5,230,623 | 7/1993 | Guthrie et al. | 433/72 |
| 5,231,483 | 7/1993 | Sieber et al. | 358/125 |
| 5,255,352 | 10/1993 | Falk et al. | 395/125 |
| 5,261,404 | 11/1993 | Mick et al. | 128/653.1 |
| 5,274,551 | 12/1993 | Corby, Jr. | 364/413.13 |
| 5,291,889 | 3/1994 | Kenet et al. | 128/653.1 |
| 5,295,199 | 3/1994 | Shino | 382/41 |
| 5,297,215 | 3/1994 | Yamagishi | 382/6 |
| 5,319,551 | 6/1994 | Sekiguchi et al. | 364/413.19 |
| 5,329,310 | 7/1994 | Liljegren et al. | 348/147 |
| 5,363,476 | 11/1994 | Kurashige et al. | 395/125 |
| 5,378,915 | 1/1995 | Hines et al. | 250/369 |
| 5,383,454 | 1/1995 | Bucholz | 128/653.1 |
| 5,384,594 | 1/1995 | Sieber et al. | 348/169 |
| 5,398,584 | 3/1995 | Hardy | 128/653.1 |
| 5,417,210 | 5/1995 | Funda et al. | 128/653.1 |
| 5,447,154 | 9/1995 | Cinquin et al. | 128/653.1 |
| 5,448,587 | 9/1995 | Hoogerhyde et al. | 395/125 |
| 5,461,706 | 10/1995 | Trow et al. | 395/125 |
| 5,491,510 | 2/1996 | Gove | 348/77 |
| 5,493,595 | 2/1996 | Schoolman | 378/41 |
| 5,497,452 | 3/1996 | Shimizu et al. | 395/120 |
| 5,511,153 | 4/1996 | Azarbayejani et al. | 395/119 |
| 5,526,812 | 6/1996 | Dumoulin et al. | 128/653.1 |
| 5,526,814 | 6/1996 | Cline et al. | 128/653.2 |
| 5,531,227 | 7/1996 | Schneider | 128/653.1 |
| 5,537,638 | 7/1996 | Morita et al. | 395/125 |
| 5,558,619 | 9/1996 | Kami et al. | 600/146 |

OTHER PUBLICATIONS

Weisburn et al., "An interactive graphics editor for 3D surgical simulation", SPIE vol. 626 Medicine XIV/PACS IV (1986), pp. 483–490.

Shalev et al., "Pseudo–3D imaging with the DICON–8", SPIE vol. 555 Madical Imaging and Instrumentation '85 (1985), pp. 63–66.

Fowler, "Computers May Drive Revolution in Neurosurgery Techniques", Washington Post, Science, Aug. 15, 1994.

Applicants' "IRA Magaziner Demo (See™)", displayed Jun. 1993 (24 minutes).

ANATOMICAL VISUALIZATION SYSTEM

This is continuation of U.S. patent application Ser. No. 08/489,061, filed Jun. 9, 1995 now abandoned by Steven D. Pieper for ANATOMICAL VISUALIZATION SYSTEM, which application is in turn a continuation-in-part of U.S. patent application Ser. No. 08/457,692, filed Jun. 1, 1995 by Michael A. McKenna, David T. Chen and Steven D. Pieper for ANATOMICAL VISUALIZATION SYSTEM, now issued as U.S. Pat. No. 5,737,506.

FIELD OF THE INVENTION

This invention relates to medical apparatus in general, and more particularly to anatomical visualization systems.

Background Of The Invention

Many medical procedures must be carried out at an interior anatomical site which is normally hidden from the view of the physician. In these situations, the physician typically uses some sort of scanning device to examine the patient's anatomy at the interior site prior to, and in preparation for, conducting the actual medical procedure. Such scanning devices typically include CT scanners, MRI devices, X-ray machines, ultrasound devices and the like, and essentially serve to provide the physician with some sort of visualization of the patient's interior anatomical structure prior to commencing the actual medical procedure. The physician can then use this information to plan the medical procedure in advance, taking into account patient-specific anatomical structure. In addition, the physician can also use the information obtained from such preliminary scanning to more precisely identify the location of selected structures (e.g., tumors and the like) which may themselves be located within the interior of internal organs or other internal body structures. As a result, the physician can more easily "zero in" on such selected structures during the subsequent medical procedure. Furthermore, in many cases, the anatomical structures of interest to the physician may be quite small and/or difficult to identify with the naked eye. In these situations, preliminary scanning of the patient's interior anatomical structure using high resolution scanning devices can help the physician locate the structures of interest during the subsequent medical procedure.

In addition to the foregoing, scanning devices of the sort described above are frequently also used in purely diagnostic procedures.

In general, scanning devices of the sort described above tend to generate two-dimensional (i.e., "2-D") images of the patient's anatomical structure. In many cases, the scanning devices are adapted to provide a set of 2-D images, with each 2-D image in the set being related to every other 2-D image in the set according to some pre-determined relationship. For example, CT scanners typically generate a series of 2-D images, with each 2-D image corresponding to a specific plane or "slice" taken through the patient's anatomical structure. Furthermore, with many scanning devices, the angle and spacing between adjacent image planes or slices is very well defined, e.g., each image plane or slice may be set parallel to every other image plane or slice, and adjacent image planes or slices may be spaced a pre-determined distance apart. By way of example, the parallel image planes might be set 1 mm apart.

In a system of the sort just described, the physician can view each 2-D image individually and, by viewing a series of 2-D images in proper sequence, can mentally generate a three-dimensional (i.e., "3-D") impression of the patient's interior anatomical structure.

Some scanning devices include, as part of their basic system, associated computer hardware and software for building a 3-D database of the patient's scanned anatomical structure using a plurality of the aforementioned 2-D images. For example, some CT and MRI scanners include such associated computer hardware and software as part of their basic system. Alternatively, such associated computer hardware and software may be provided independently of the scanning devices, as a sort of "add-on" to the system; in this case, the data from the scanned 2-D images is fed from the scanning device to the associated computer hardware and software in a separate step. In either case, a trained operator using the scanning device can create a set of scanned 2-D images, assemble the data from these scanned 2-D images into a 3-D database of the scanned anatomical structure, and then generate various additional images of the scanned anatomical structure using the 3-D database. This feature is a very powerful tool, since it essentially permits a physician to view the patient's scanned anatomical structure from a wide variety of different viewing positions. As a result, the physician's understanding of the patient's scanned anatomical structure is generally greatly enhanced.

In addition, these systems often include software and/or hardware tools to allow measurements to be made, e.g., the length of lines drawn on the image may be calculated.

While the 2-D slice images generated by the aforementioned scanning devices, and/or the 3-D database images generated by the aforementioned associated computer hardware and software, are generally of great benefit to physicians, certain significant limitations still exist.

For one thing, with current systems, each scanned 2-D slice image is displayed as a separate and distinct image, and each image generated from the 3-D database is displayed as a separate and distinct image. Unfortunately, physicians can sometimes have difficulty correlating what they see on a particular scanned 2-D slice image with what they see on a particular image generated from the 3-D database.

For another thing, in many situations a physician may be viewing images of a patient's scanned anatomical structure in preparation for conducting a subsequent medical procedure in which a prosthetic device must be fitted in the patient. In these situations it can be relatively difficult and/or time-consuming for the physician to accurately measure and record all of the anatomical dimensions needed for proper sizing of the prosthetic device to the patient. By way of example, in certain situations a patient may develop an abdominal aortic aneurysm ("AAA") in the vicinity of the aorta's iliac branching, and replacement of the affected vascular structure may be indicated. In this case it is extremely important for the physician to determine, for each affected portion of blood vessel, accurate length and cross-sectional dimensions to ensure proper sizing of the replacement prosthesis to the patient. Such anatomical measurement and recordation can be difficult and/or time-consuming with existing visualization systems. This has proven to be particulary true when dealing with anatomical structures which have a tortuous path or branching structure, e.g., blood vessels.

Objects Of The Present Invention

Accordingly, one object of the present invention is to provide an improved anatomical visualization system wherein a scanned 2-D slice image can be appropriately combined with an image generated from a 3-D database so as to create a single composite image.

Another object of the present invention is to provide an improved anatomical visualization system wherein a marker can be placed onto a 2-D slice image displayed on a screen, and this marker will be automatically incorporated, as appropriate, into a 3-D computer model maintained by the system, as well as into any other 2-D slice image data maintained by the system.

Still another object of the present invention is to provide an improved anatomical visualization system wherein a margin of pre-determined size can be associated with a marker of the sort described above, and further wherein the margin will be automatically incorporated into the 3-D computer model, and into any other 2-D slice image data, in association with that marker.

Yet another object of the present invention is to provide an improved anatomical visualization system wherein the periphery of objects contained in a 3-D computer model maintained by the system can be automatically identified in any 2-D slice image data maintained by the system, wherein the periphery of such objects can be highlighted as appropriate in 2-D slice images displayed by the system.

And another object of the present invention is to provide an improved method for visualizing anatomical structure.

Another object of the present invention is to provide an improved anatomical visualization system wherein patient-specific anatomical dimensions may be easily and quickly determined.

And another object of the present invention is to provide an improved anatomical visualization system wherein an appropriate set of scanned 2-D images can be assembled into a 3-D database, computer models of patient-specific anatomical structures can be extracted from the information contained in this 3-D database, and these computer models can then be used to calculate desired patient-specific anatomical dimensions.

Still another object of the present invention is to provide an improved anatomical visualization system which is particularly well adapted to determine patient-specific anatomical dimensions for structures which have a branching configuration, e.g., blood vessels.

Yet another object of the present invention is to provide an improved method for calculating patient-specific anatomical dimensions using appropriate scanned 2-D image data.

SUMMARY OF THE INVENTION

These and other objects are addressed by the present invention, which comprises a visualization system comprising a first database that comprises a plurality of 2-D slice images generated by scanning a structure. The 2-D slice images are stored in a first data format. A second database is also provided that comprises a 3-D computer model of the scanned structure. The 3-D computer model comprises a first software object that is defined by a 3-D geometry database. Means are provided for inserting a second software object into the 3-D computer model so as to augment the 3-D computer model. The second software object is also defined by a 3-D geometry database, and includes a planar surface. Means for determining the specific 2-D slice image associated with the position of the planar surface of the second software object within the augmented 3-D computer model are provided in a preferred embodiment of the invention. Means are also provided for texture mapping the specific 2-D slice image onto the planar surface of the second software object. Display means are provided for displaying an image of the augmented 3-D computer model so as to simultaneously provide a view of the first software object and the specific 2-D slice image texture mapped onto the planar surface of the second software object.

In one alternative embodiment of the present invention, a visualization system is provided comprising a first database comprising a plurality of 2-D slice images generated by scanning a structure. The 2-D slice images are again stored in a first data format. A second database comprising a 3-D computer model of the scanned structure is also provided in which the 3-D computer model comprises a first software object that is defined by a 3-D geometry database. Means are provided for selecting a particular 2-D slice image the first database. Means are also provided for inserting a second software object into the 3-D computer model so as to augment the 3-D computer model. The second software object is defined by a 3-D geometry database, and also includes a planar surface. In this alternative embodiment however, the second software object is inserted into the 3-D computer model at the position corresponding to the position of the selected 2-D slice image relative to the scanned structure. Means for texture mapping the specific 2-D slice image onto the planar surface of the second software object are also provides. Means are provided for displaying an image of the augmented 3-D computer model so as to simultaneously provide a view of the first software object and the specific 2-D slice image texture mapped onto the planar surface of the second software object.

In each of the foregoing embodiments of the present invention, the 3-D geometry database may comprise a surface model. Likewise, the system may further comprise means for inserting a marker into the first database, whereby the marker will be automatically incorporated into the second database, and further wherein the marker will be automatically displayed where appropriate in any image displayed by the system. Also, the system may further comprise a margin of pre-determined size associated with the marker. Additionally, the system may further comprise means for automatically determining the periphery of any objects contained in the second database and for identifying the corresponding data points in the first database, whereby the periphery of such objects can be highlighted as appropriate in any image displayed by the system. Often, the scanned structure will comprise an anatomical structure.

The present invention also comprises a method for visualizing an anatomical structure.

In yet another form of the present invention, the visualization system may incorporate means for determining patient-specific anatomical dimensions using appropriate scanned 2-D image data. More particularly, the visualization system may include means for assembling an appropriate set of scanned 2-D images into a 3-D database, means for extracting computer models of patient-specific anatomical structures from the information contained in the 3-D database, and means for calculating desired patient-specific anatomical dimensions from the aforementioned computer models.

The present invention also comprises a method for calculating patient-specific anatomical dimensions using appropriate scanned 2-D image data. In one form of the present invention, the method comprises the steps of (1) assembling an appropriate set of scanned 2-D images into a 3-D database; (2) extracting computer models of patient-specific anatomical structures from the information contained in the 3-D database, and (3) calculating desired patient-specific anatomical dimensions from the aforementioned computer models.

In a more particular form of the present invention, the visualization system is particularly well adapted to determine patient-specific anatomical dimensions for structures which have a branching configuration, e.g., blood vessels. In this form of the invention, the visualization system is adapted to facilitate (1) assembling an appropriate set of scanned 2-D images into a 3-D database; (2) segmenting the volumetric data contained in the 3-D database into a set of 3-D locations corresponding to the specific anatomical structure to be measured; (3) specifying, for each branching structure contained within the specific anatomical structure of interest, a branch line in the volumetric data set that uniquely indicates that branch structure, with the branch line being specified by selecting appropriate start and end locations on two of the set of scanned 2-D images; (4) calculating, for each branching structure contained within the specific anatomical structure of interest, a centroid path in the volumetric data set for that branching structure, with the centroid path being determined by calculating, for each scanned 2-D image corresponding to the branch line, the centroid for the branch structure contained in that particular scanned 2-D image; (5) applying a curve-fitting algorithm to the centroid paths determined above so as to supply data for any portions of the anatomical structure which may lie between the aforementioned branch lines, and for "smoothing out" any noise that may occur in the system; and (6) applying known techniques to the resulting space curves so as to determine the desired anatomical dimensions.

BRIEF DESCRIPTION OF THE DRAWINGS

These and other objects and features of the present invention will be more fully disclosed or rendered obvious by the following detailed description of the preferred embodiment of the invention, which is to be considered together with the accompanying drawings wherein like numbers refer to like parts, and further wherein.

DETAILED DESCRIPTION OF THE PREFERRED EMBODIMENT

Figure 1:
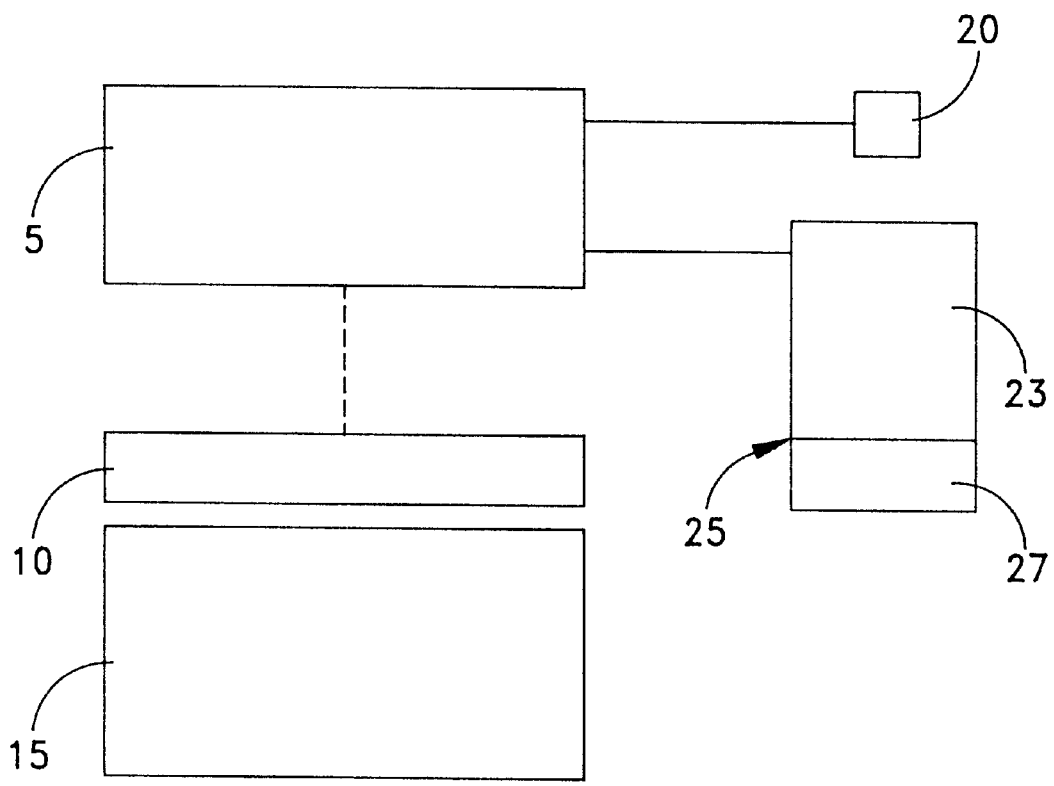
FIG. 1 is a schematic view showing a scanning device generating a set of 2-D images of the anatomy of a patient.

Looking first at FIG. 1, a scanning device 5 is shown as it scans the interior anatomical structure of a patient 10, as that patient 10 lies on a scanning platform 15.

Scanning device 5 is of the sort adapted to generate scanning data corresponding to a series of 2-D images, where each 2-D image corresponds to a specific viewing plane or "slice" taken through the patient's body. Furthermore, scanning device 5 is adapted so that the angle and spacing between adjacent image planes or slices can be very well defined, e.g., each image plane or slice may be set parallel to every other image plane or slice, and adjacent image planes or slices may be spaced a pre-determined distance apart. By way of example, the parallel image planes might be set 1 mm apart.

The scanning data obtained by scanning device 5 can be displayed as a 2-D slice image on a display 20, and/or it can be stored in its 2-D slice image data form in a first section 23 of a data storage device or medium 25. Furthermore, additional information associated with the scanning data (e.g. patient name, age, etc.) can be stored in a second section 27 of data storage device or medium 25.

By way of example, scanning device 5 might comprise a CT scanner of the sort manufactured by GE Medical Systems of Milwaukee, Wis.

Figure 2:
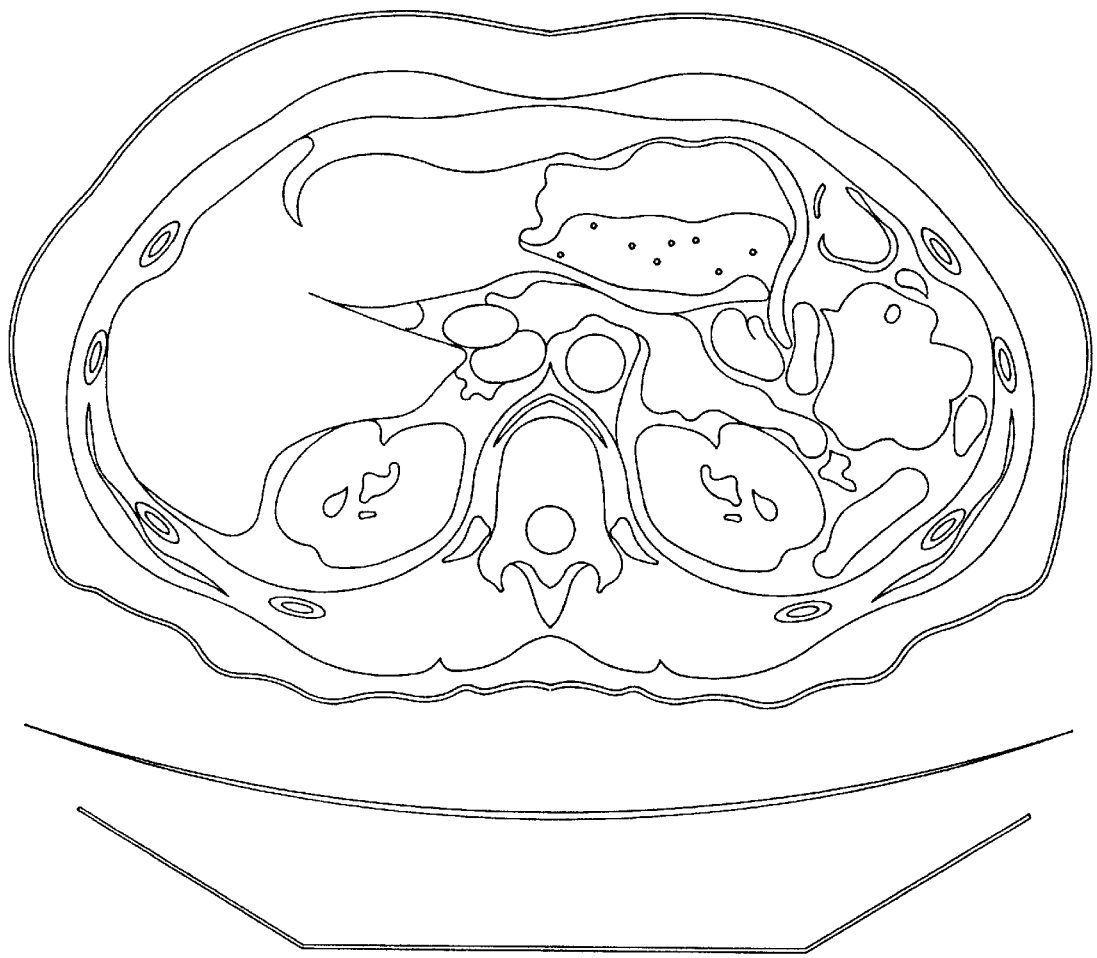
FIG. 2 is a 2-D slice image corresponding to an axial slice taken through the abdomen of an individual.

By way of further example, a 2-D slice image of the sort generated by scanning device 5 and displayed on display 20 might comprise the 2-D slice image shown in FIG. 2. In the particular example shown in FIG. 2, the 2-D slice image shown corresponds to an axial slice taken through an individual's abdomen and showing, among other things, that individual's liver.

Scanning device 5 may format its scanning data in any one of a number of different data structures. By way of example, scanning device 5 might format its scanning data in the particular data format used by a CT scanner of the sort manufactured by GE Medical Systems of Milwaukee, Wis. More specifically, with such a scanning device, the scanning data is generally held as a series of data "frames", where each data frame corresponds to a particular 2-D slice image taken through the patient's body. Furthermore, within each data frame, the scanning data is generally organized so as to represent the scanned anatomical structure at a particular location within that 2-D slice image. Such a data structure is fairly common for scanning devices of the sort associated with the present invention. However, it should be appreciated that the present invention is not dependent on the particlar data format utilized by scanning device 5. For the purposes of the present invention, the scanning data provided by scanning device 5 can be formatted in almost any desired data structure, so long as that data structure is well defined, whereby the scanning data can be retrieved and utilized as will hereinafter be disclosed in further detail.

Figure 3:
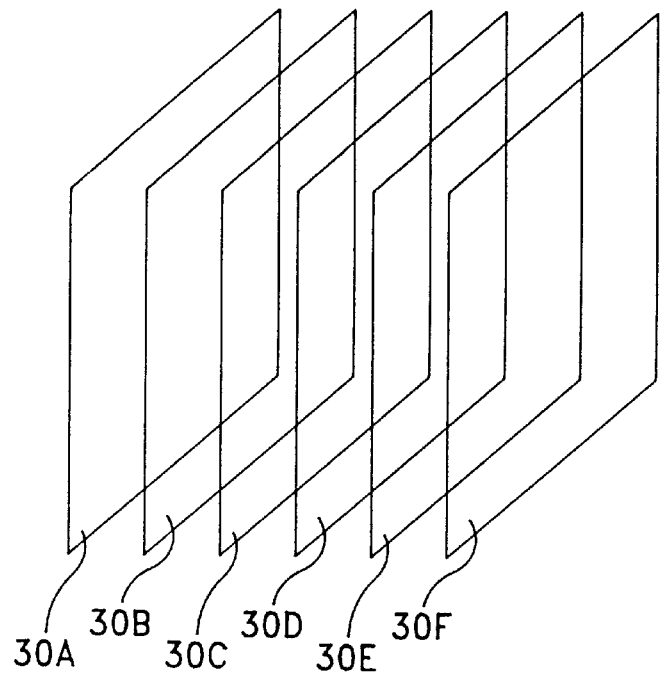
FIG. 3 shows a series of data frames corresponding to 2-D slice images arranged in a parallel array.
Figure 4:
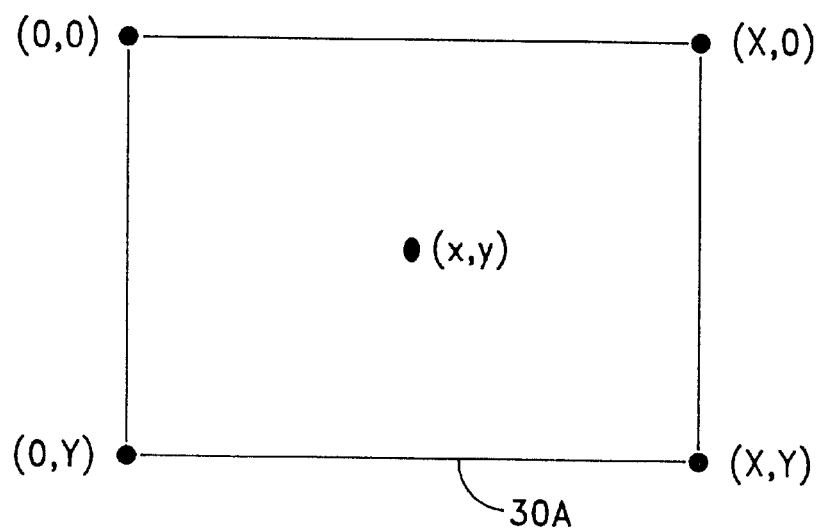
FIG. 4 is a schematic view showing the scanning data contained within an exemplary data frame.

For purposes of illustrating the present invention, it can be convenient to think of the scanning data generated by scanning device 5 as being organized in the data structures schematically illustrated in FIGS. 3 and 4.

More particularly, in FIG. 3, a series of data frames 30A, 30B, 30C, etc. are shown arranged in a parallel array. Each of these data frames 30A, 30B, 30C, etc. corresponds to a particular 2-D slice image taken through the patient's body by scanning device 5, where the 2-D slice images are taken parallel to one another. In addition, adjacent image planes or slices are spaced apart by a constant, pre-determined distance, e.g., 1 mm.

Furthermore, in FIG. 4, the scanning data contained within an exemplary data frame 30A is shown represented in an X-Y coordinate scheme so as to quickly and easily identify the scanned anatomical structure disposed at a particular location within that 2-D slice image. Typically, the scanning data relating to a particular X-Y coordinate represents an image intensity value. This image intensity value generally reflects some attribute of the specific anatomical structure being scanned, e.g., the tissue density.

As noted above, the scanning data generated by scanning device 5 is stored in its 2-D slice image data form in first section 23 of data storage device or medium 25, with the scanning data being stored in a particular data format as determined by the manufacturer of scanning device 5.

Figure 5:
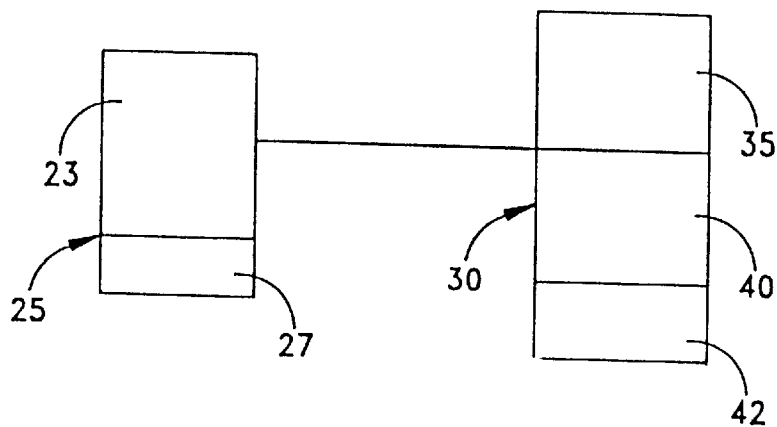
FIG. 5 shows scanning data stored in a first storage device or medium being retrieved, processed and then stored again in a second data storage device or medium.

In accordance with the present invention, and looking now at Fig.5, the scanning data stored in first section 23 of data storage device or medium 25 is retrieved, processed and then stored again in a data storage device or medium 30.

More particularly, the scanning data stored in first section 23 of data storage device or medium 25 is retrieved and processed so as to convert the scanning data generated by scanning device 5 from its 2-D slice image data form into a 3-D computer model of the patient's anatomical structure. This 3-D computer model is then stored in a first section 35 of data storage device or medium 30.

In addition, the scanning data stored in first section 23 of data storage device or medium 25 is retrieved and processed as necessary so as to convert the scanning data into a preferred data format for the 2-D slice image data. The 2-D slice image data is then stored in this preferred data format in second section 40 of data storage device or medium 30.

Furthermore, the additional information associated with the scanning data (e.g. patient name, age, etc.) which was previously stored in second section 27 of data storage device or medium 25 can be stored in a third section 42 of data storage device or medium 30.

In accordance with the present invention, once the 3-D computer model has been stored in first section 35 of data storage device or medium 30, and the 2-D slice image data has been stored in a preferred data format in second section 40 of data storage device or medium 30, a physician can then use an appropriately programmed computer to access the 3-D computer model stored in first section 35 of data storage device or medium 30, and/or the 2-D slice image data stored in second section 40 of data storage device or medium 30, to generate desired patient-specific images.

Figure 6:
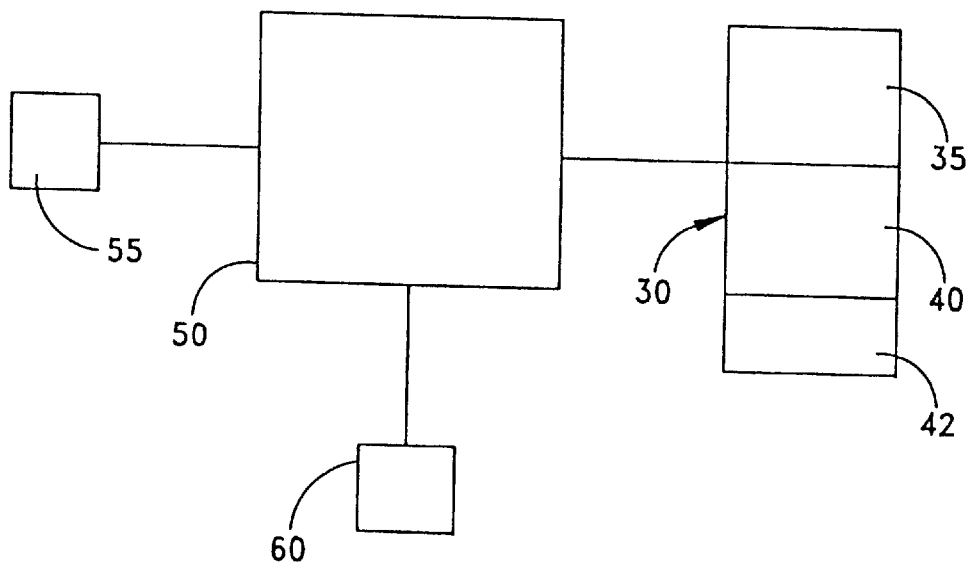
FIG. 6 is a schematic view of a system for retrieving and viewing scanning data.

More particularly, and looking now at FIG. 6, once the 3-D computer model has been stored in first section 35 of data storage device or medium 30, and the 2-D slice image data has been stored in a preferred data format in second section 40 of data storage device or medium 30, a physician can use an appropriately programmed computer 50, operated by input devices 55, to access the 3-D computer model stored in first section 35 of data storage device or medium 30, and/or the 2-D slice image data stored in second section 40 of data storage device or medium 30, so as to generate the desired patient-specific images and display those images on a display 60.

To this end, it will be appreciated that the specific data structure used to store the 3-D computer model in first section 35 of data storage device or medium 30, and the specific data structure used to store the 2-D slice image data in second section 40 of data storage device or medium 30, will depend on the specific nature of computer 50 and on the particular operating system and application software being run on computer 50.

Figure 7:
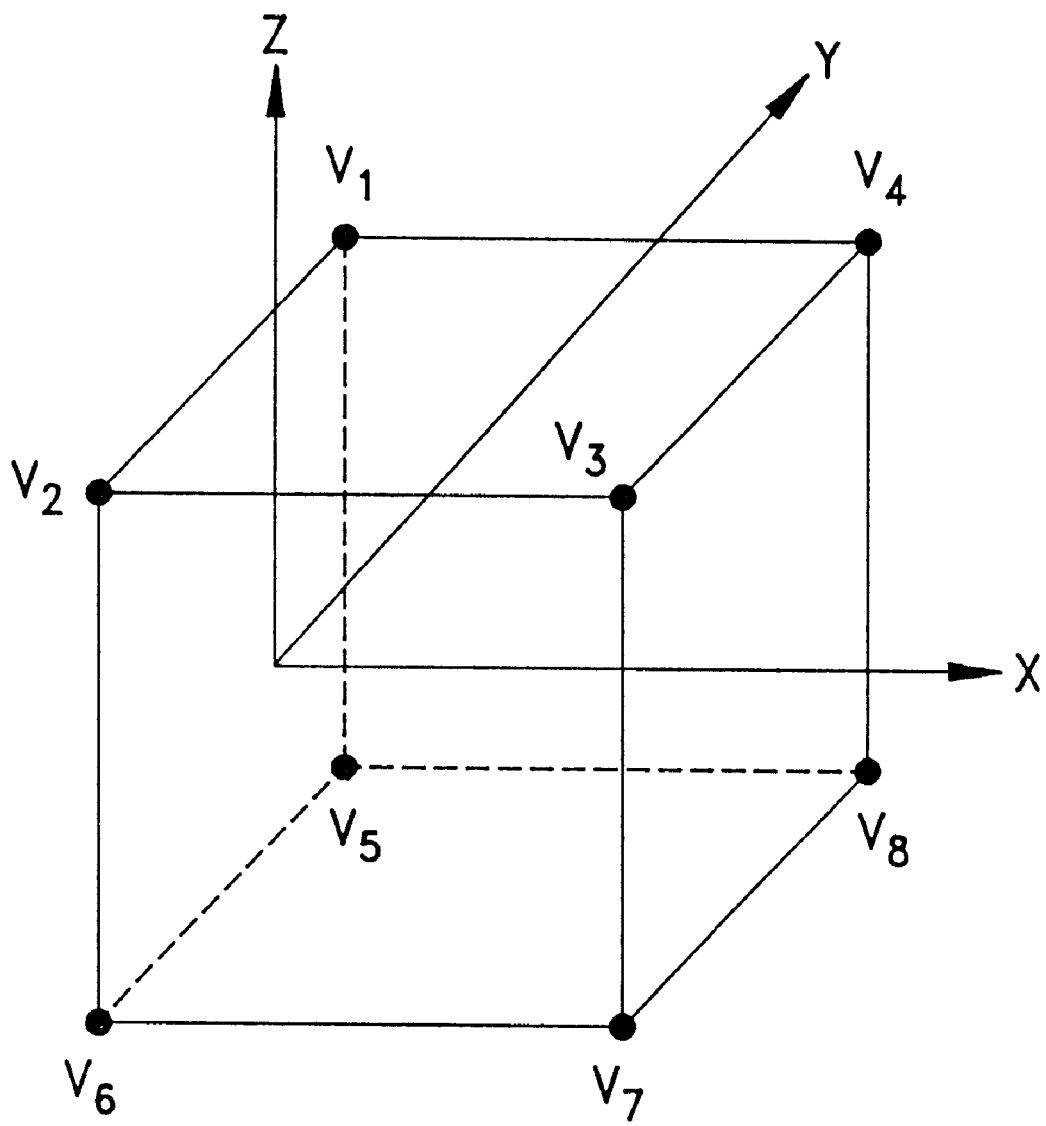
FIG. 7 is a schematic view of a unit cube for use in defining polygonal surface models.
Figure 8:
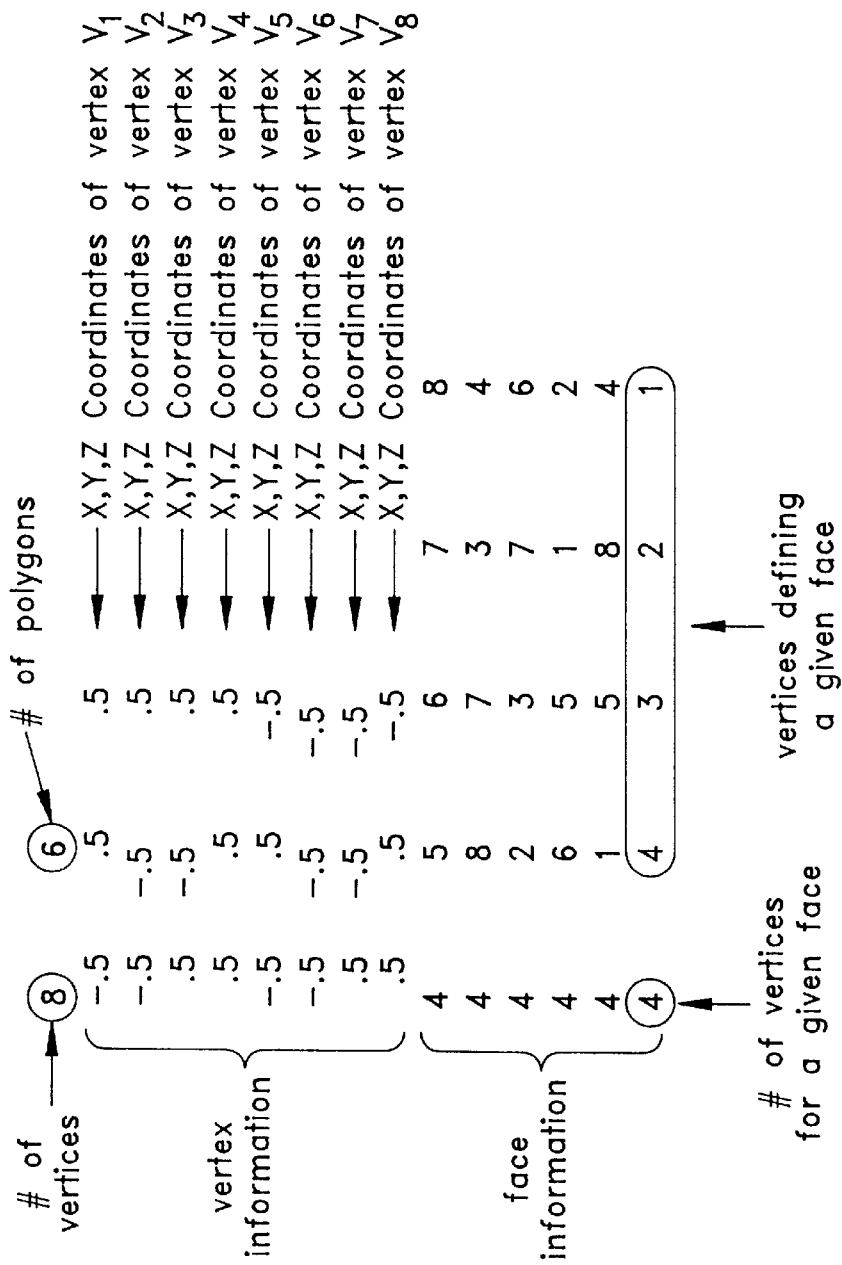
FIG. 8 illustrates the data file format of the polygonal surface model for the simple unit cube shown in FIG. 7.
Figure 9A:
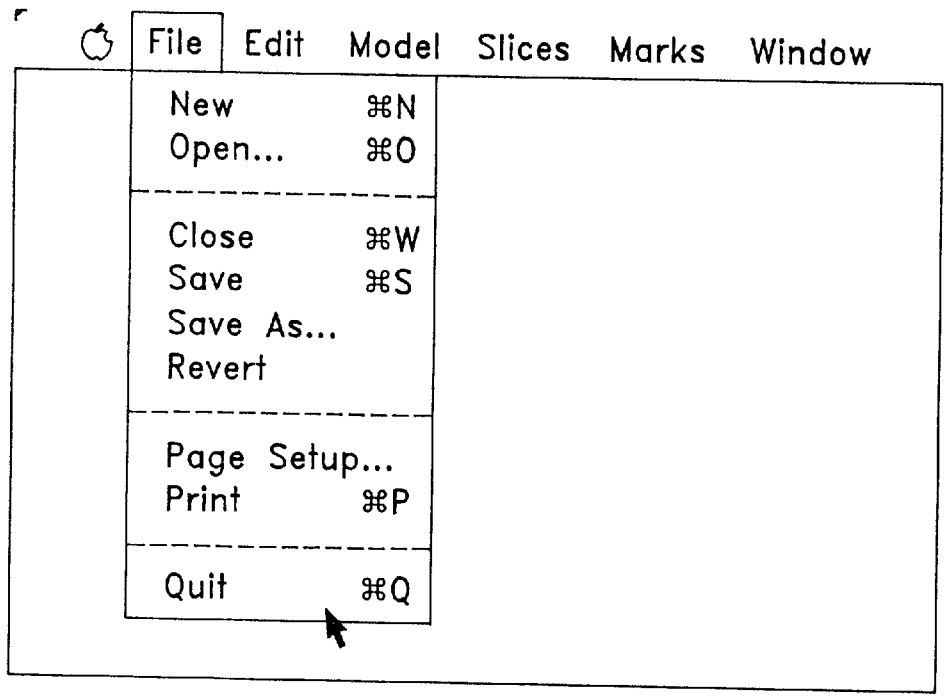
FIGS. 9A–9F illustrate a variety of menu choices which may be utilized in connection with the present invention.
Figure 9B:
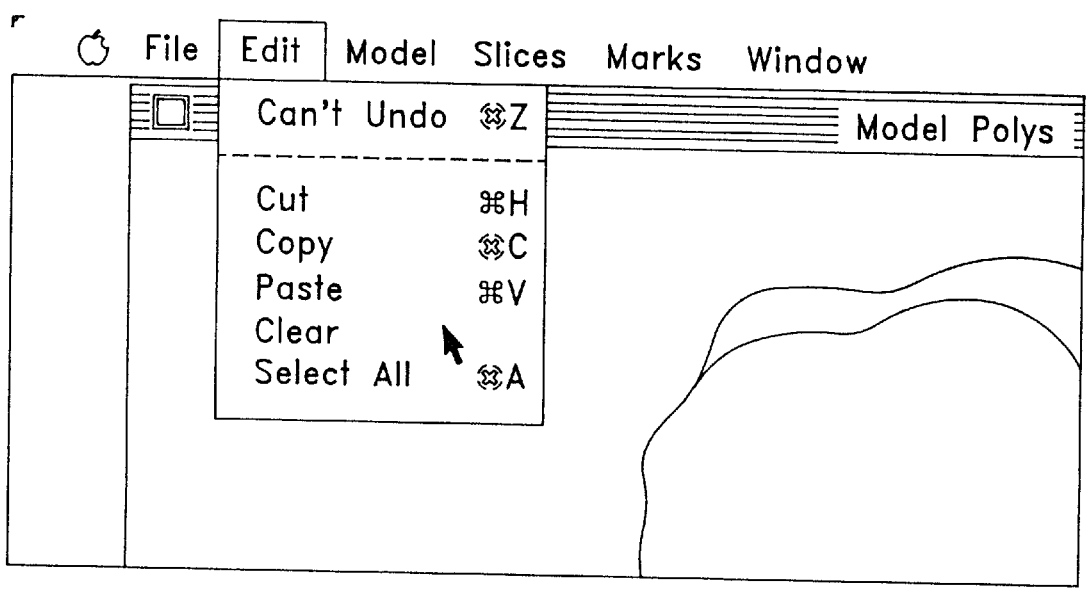
Figure 9C:
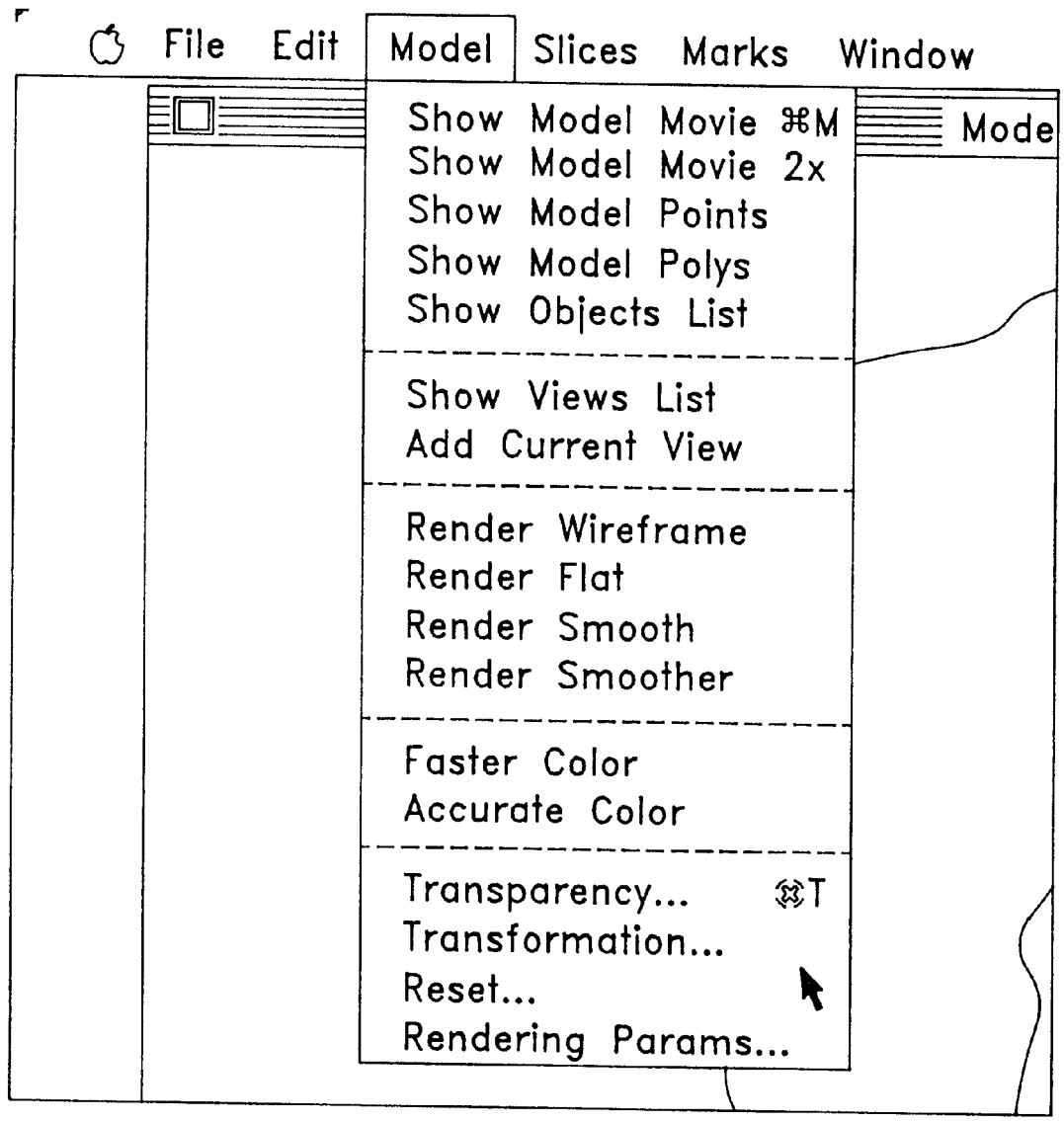
Figure 9D:
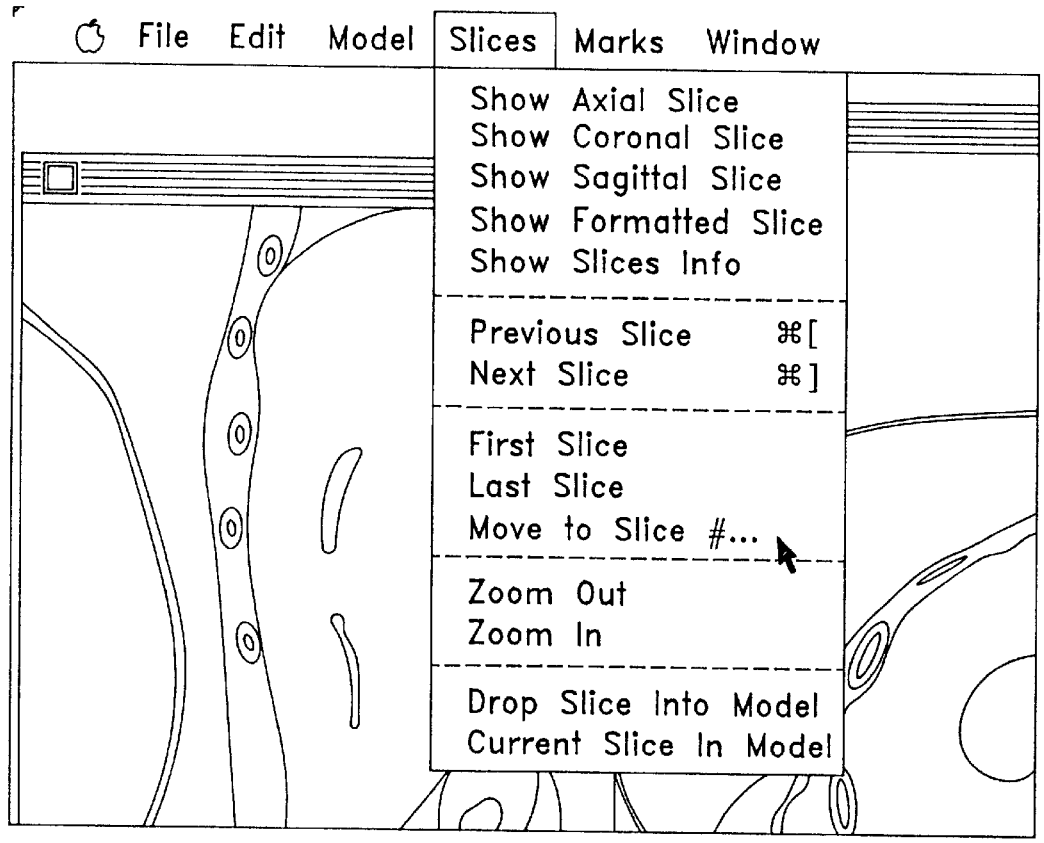
Figure 9E:
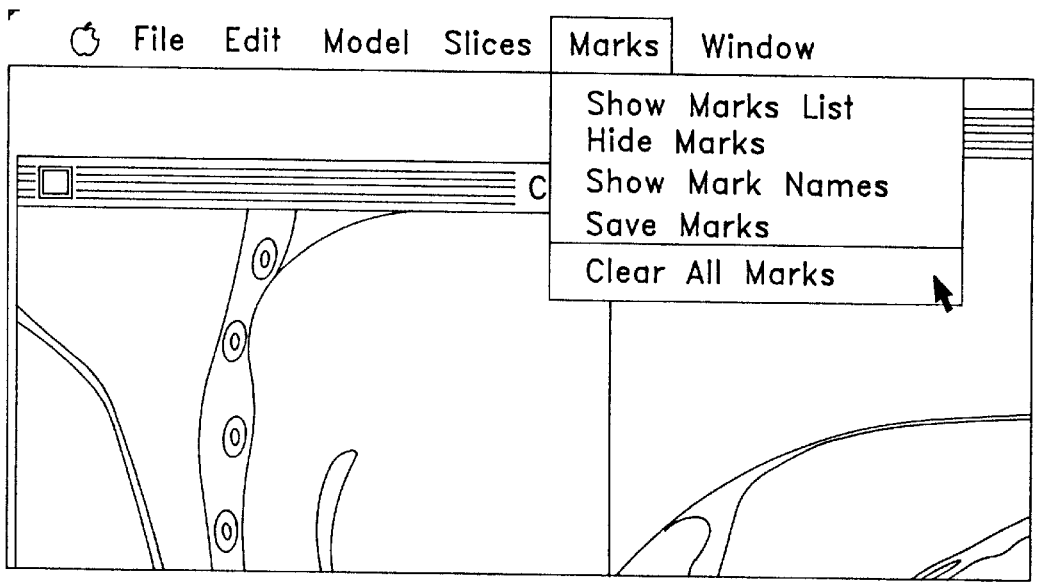
Figure 9F:
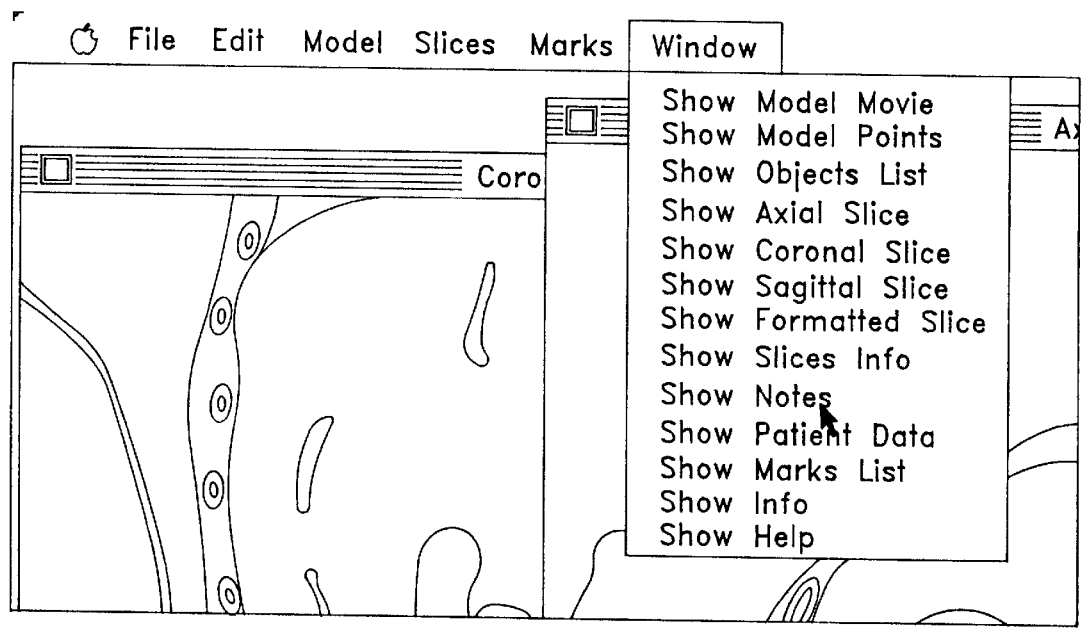

In general, however, the 3-D computer model contained in first section 35 of data storage device or medium 30 is preferably structured as a collection of software objects, with each software object being defined by a polygonal surface model of the sort well known in the art. By way of example, a scanned anatomical structure such as a human liver might be modeled as three distinct software objects, with the outer surface of the general mass of the liver being one software object, the outer surface of the vascular structure of the liver being a second software object, and the outer surface of a tumor located in the liver being a third software object. By way of further example, FIGS. 7 and 8 illustrate a typical manner of defining a software object by a polygonal surface model. In particular, FIG. 7 illustrates the vertices of a unit cube set in an X-Y-Z coordinate system, and FIG. 8 illustrates the data file format of the polygonal surface model for this simple unit cube. As is well known in the art, more complex shapes such as human anatomical structure can be expressed in corresponding terms.

Furthermore, the 3-D computer model contained in first section 35 of data storage device or medium 30 is created by analyzing the 2-D slice image data stored in first section 23 of data storage device or medium 25 using techniques well known in the art. For example, the 2-D slice image data stored in first section 23 of data storage device or medium 25 might be processed using the well known "Marching Cubes" algorithm, which is a so-called "brute force" surface construction algorithm that extracts isodensity surfaces from volume data, producing from one to five triangles within voxels that contain the surface. Alternatively, the 2-D slice image data stored in first section 23 of data storage device or medium 25 might be processed into the 3-D computer model stored in first section 35 of data storage device or medium 30 by some other appropriate modelling algorithm so as to yield the desired 3-D computer model.

As noted above, the specific data structure used to store the 2-D slice image data in second section 40 of data storage device or medium 30 will also depend on the specific nature of computer 50 and on the particular operating system and application software being run on computer 50.

In general, however, the 2-D slice image data contained in second section 40 of data storage device or medium 30 is preferably structured as a series of data "frames", where each data frame corresponds to a particular 2-D slice image taken through the patient's body, and where the scanning data within each data frame is organized so as to represent the scanned anatomical structure at a particular location within that 2-D slice image.

In the present invention, it is preferred that computer 50 comprise a Power PC-based, Macintosh operating system ("Mac OS") type of computer, e.g. a Power PC Macintosh 8100/80 of the sort manufactured by Apple Computer, Inc. of Cupertino, California. In addition, it is preferred that computer 50 be running Macintosh operating system software, e.g. Mac OS Ver. 7.5.1, such that computer 50 can readily access a 3-D computer model formatted in Apple's well-known QuickDraw 3D data format and display images generated from that 3D computer model, and such that computer 50 can readily access and display 2-D images formatted in Apple's well-known QuickTime image data format. Input devices 55 preferably comprise the usual computer input devices associated with a Power PC-based, Macintosh operating system computer, e.g., input devices 55 preferably comprise a keyboard, a mouse, etc.

In view of the foregoing, in the present invention it is also preferred that the 3-D computer model contained in first section 35 of data storage device or medium 30 be formatted in Apple's QuickDraw 3D data format, whereby the Mac OS computer 50 can quickly and easily access the 3-D computer model contained in first section 35 of data storage device or medium 30 and display images generated from that 3-D computer model on display 60.

In view of the foregoing, in the present invention it is also preferred that the 2-D slice image data contained in second section 40 of data storage device or medium 30 be formatted in Apple's QuickTime image data format. In this way computer 50 can quickly and easily display the scanned 2-D slice images obtained by scanning device 5. It will be appreciated that, to the extent that scanning device 5 happens to format its scanning data in the preferred QuickTime image data format, no reformatting of the 2-D slice image data will be necessary prior to storing the 2-D slice image data in second section 40 of data storage device or medium 30. However, to the extent that scanning device 5 happens to format its scanning data in a different data structure, reformatting of the 2-D slice image data will be necessary so as to put it into the preferred QuickTime image data format. Such image data reformatting is of the sort well known in the art.

As a result of the foregoing, it will be seen that a physician operating computer 50 through input devices 55 can generate a desired image from the 3-D computer model contained within first section 35 of data storage device or medium 30. In particular, the physician can use input devices 55 to (1) open a window on display 60, (2) instruct the computer as to the desired angle of view, (3) generate the corresponding image of the scanned anatomical structure from the desired angle of view, using the 3-D computer model contained within first section 35 of data storage device or medium 30, and (4) display that image in the open window on display 60.

In addition, a physician operating computer 50 through input devices 55 can display a desired 2-D slice image from the 2-D slice image data contained within second section 40 of data storage device or medium 30. In particular, the physician can use input devices 55 to (1) open a window on display 60, (2) select a particular 2-D slice image contained within second section 40 of data storage device or medium 30, and (3) display that slice image in the open window on display 60.

More particularly, and looking now at FIGS. 9A–9F, computer 50 is preferably programmed so as to provide a variety of pre-determined menu choices which may be selected by the physician operating computer 50 via input devices 55.

Figure 10:
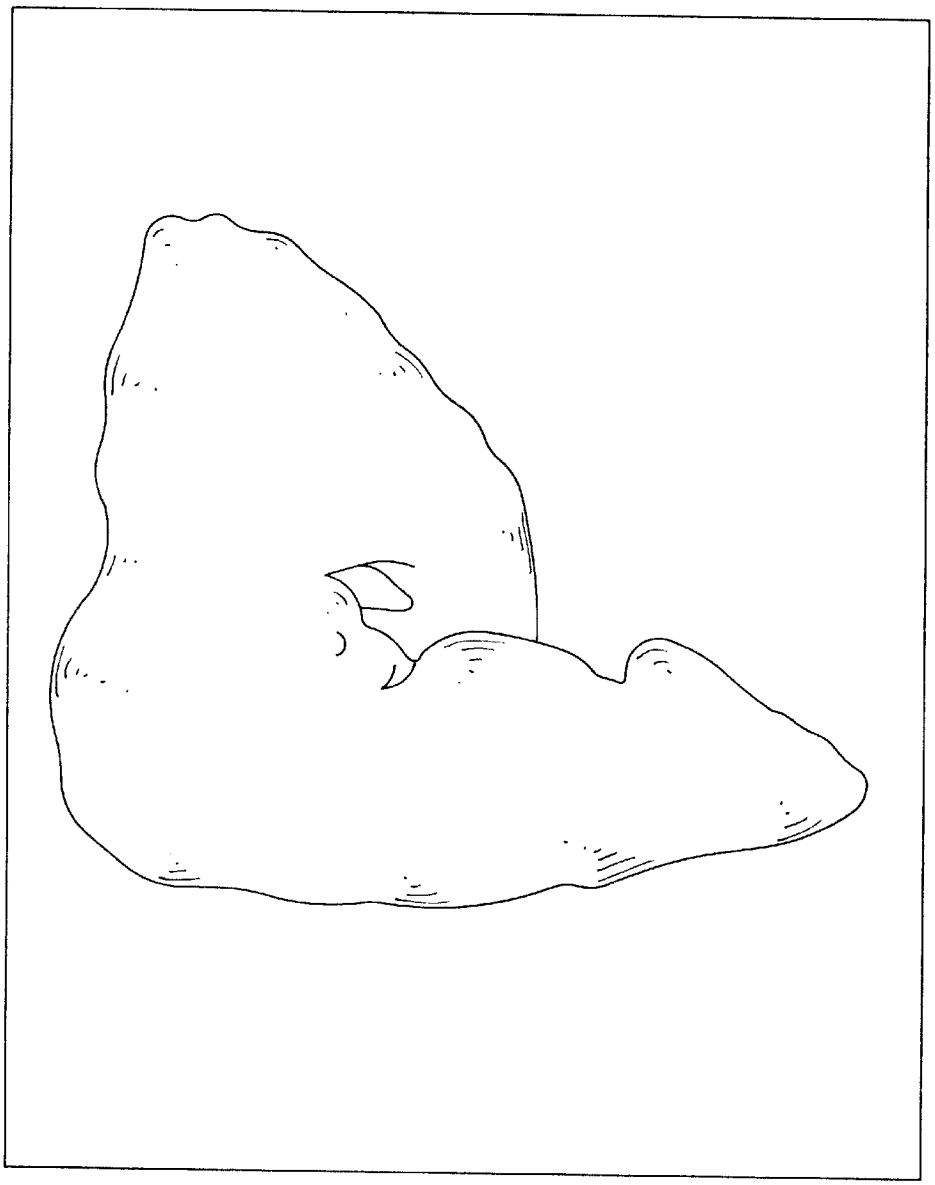
FIG. 10 illustrates an image drawn to a window using the data contained in the 3-D computer model associated with the present invention.

Thus, for example, if the physician wishes to produce a desired image from the 3-D computer model contained within first section 35 of data storage device or medium 30, the physician uses input devices 55 to invoke the command to display the 3-D computer model; the software then creates a window to display the image, it renders an image from the 3-D computer model contained within first section 35 of data storage device or medium 30, and then displays that image in the open window on display 60. By way of example, FIG. 10 illustrates an image drawn to a window using the data contained in the 3-D computer model stored in first section 35 of data storage device or medium 30. The physician can use input devices 55 to instruct the image rendering software as to the particular angle of view desired. In particular, the physician can depress a mouse key and then drag on the object so as to rotate the object into the desired angle of view. Additionally, one can also use the keyboard and mouse to move the view closer in or further out, or to translate the object side to side or up and down relative to the image plane. Programming to effect such computer operation is of the sort well known in the art.

Figure 11:
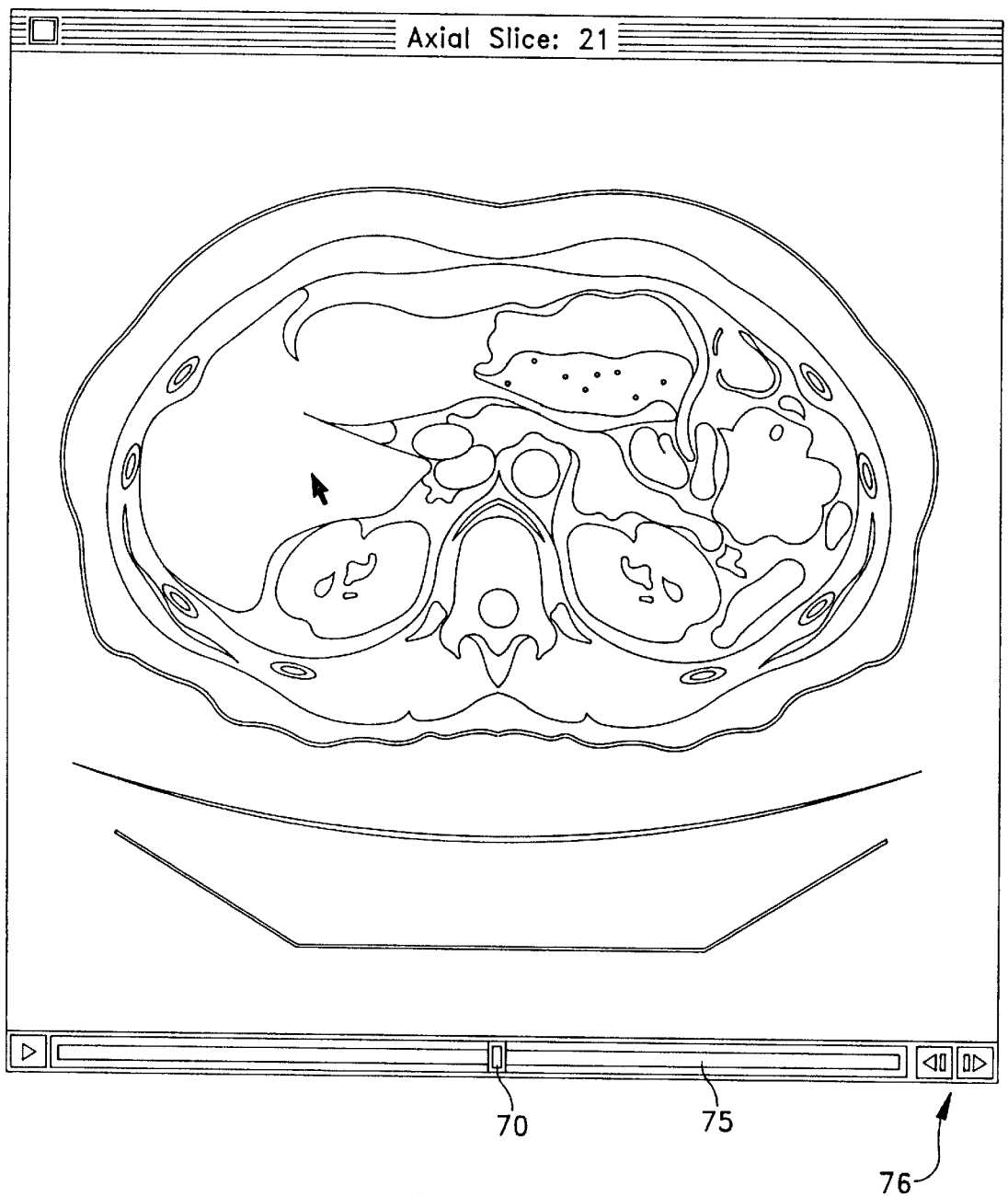
FIG. 11 illustrates a 2-D slice image drawn to a window in accordance with the present invention.

In a similar manner, the physician can use menu choices such as those shown in FIGS. 9A–9F to open a window on the display 60 to display a desired 2-D image slice from second section 40 of data storage device or medium 30 in that window. The physician can select between different image slices utilizing input devices 55. By way of example, FIG. 11 illustrates a 2-D image slice drawn to a window by the operating system using the data contained in second section 40 of data storage device or medium 30. By dragging icon 70 back and forth along slider 75, the physician can "leaf" back and forth through the collection of axial slices, i.e., in the example of FIG. 11 in which axial slice #21 is displayed, dragging icon 70 to the left might cause axial slice #20 to be displayed, and dragging icon 70 to the right might cause axial slice #22 to be displayed. Additionally, one can also step the image from the current slice number to a previous or following slice number, using menu commands or by clicking the mouse cursor on the single step icons set at the right side of slider 75. Menu commands can also be provided to change the slice window display directly to the first or last slice image in the 2-D slice image set, or to change the slice window display to a user-specified slice number. Programming to effect such computer operation is of the sort well known in the art.

Figure 12:
FIG. 12 illustrates a composite image formed from information contained in both the 3-D computer model and the 2-D image slice data structure.

As a consequence of using the aforementioned image rendering software, i.e., the Mac OS, the Apple QuickDraw 3D data format and software, and the Apple QuickTime image data format and software, or some equivalent hardware and software, it is possible to insert an additional software object into the 3-D computer model contained within first section 35 of data storage device or medium 30. In particular, it is possible to insert an additional software object having a "blank" planar surface into the 3-D computer model. Furthermore, using the computer's image rendering software, it is possible to texture map a 2-D slice image from second section 40 of data storage device or medium 30 onto the blank planar surface of the software object. Most significantly, since the 3-D computer model is created out of the same scanning data as the 2-D slice images, it is possible to determine the specific 2-D slice image associated with a given position of the blank planar surface. Accordingly, when an image is generated from the 3-D computer model, both 3-D model structure and 2-D image slice structure can be simultaneously displayed in proper registration with one another, thereby providing a single composite image of the two separate images. See, for example, FIG. 12, which shows such a composite image. Again, the physician can use input devices 55 to instruct the operating system's image rendering software as to where the aforementioned "additional" software object is to be inserted into the model and as to the particular angle of view desired. Programming to effect such computer operation is of the sort well known in the art.

In the foregoing description of the present invention, the 2-D slice image data generated by scanning device 5 has generally been discussed in the context of the standard "axial" slice images normally generated by scanning devices of the type associated with this invention. However, it is to be appreciated that it is also possible to practice the present invention in connection with sagittal or coronal 2-D slice images.

Figure 13:
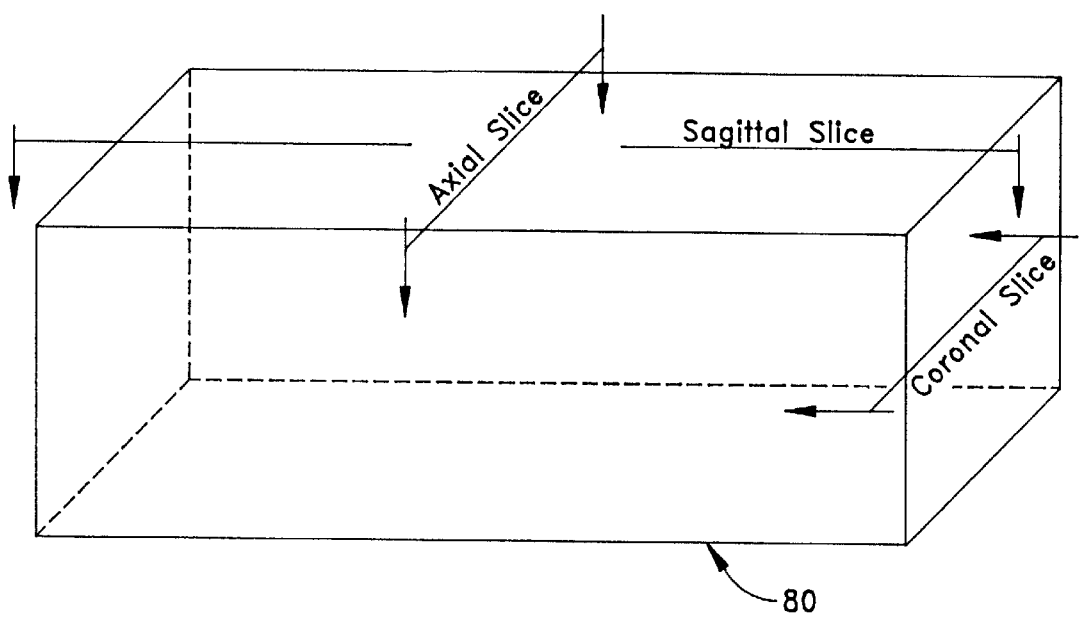
FIG. 13 is a schematic illustration showing the relationship between axial slices, sagittal slices and coronal slices.

More particularly, and looking next at FIG. 13, the relative orientation of axial, sagittal and coronal slice images are shown in the context of a schematic view of a human body 80. Scanning device 5 will normally generate axial slice image data when scanning a patent. In addition, in many cases scanning device 5 will also assemble the axial slice data into a 3-D database of the scanned anatomical structure, and then use this 3-D database to generate a corresponding set of sagittal and/or coronal 2-D slice images. In the event that scanning device 5 does not have the capability of generating the aforementioned sagittal and/or coronal 2-D slice images, these 2-D slice images may be generated from a set of the axial 2-D images in a subsequent operation, using computer hardware and software of the sort well known in the art. Alternatively, computer 50 could be programmed to render such sagittal and/or coronal 2-D slices "on the fly" from the 2-D slice image data contained in second section 40 of data storage device or medium 30.

Figure 14:
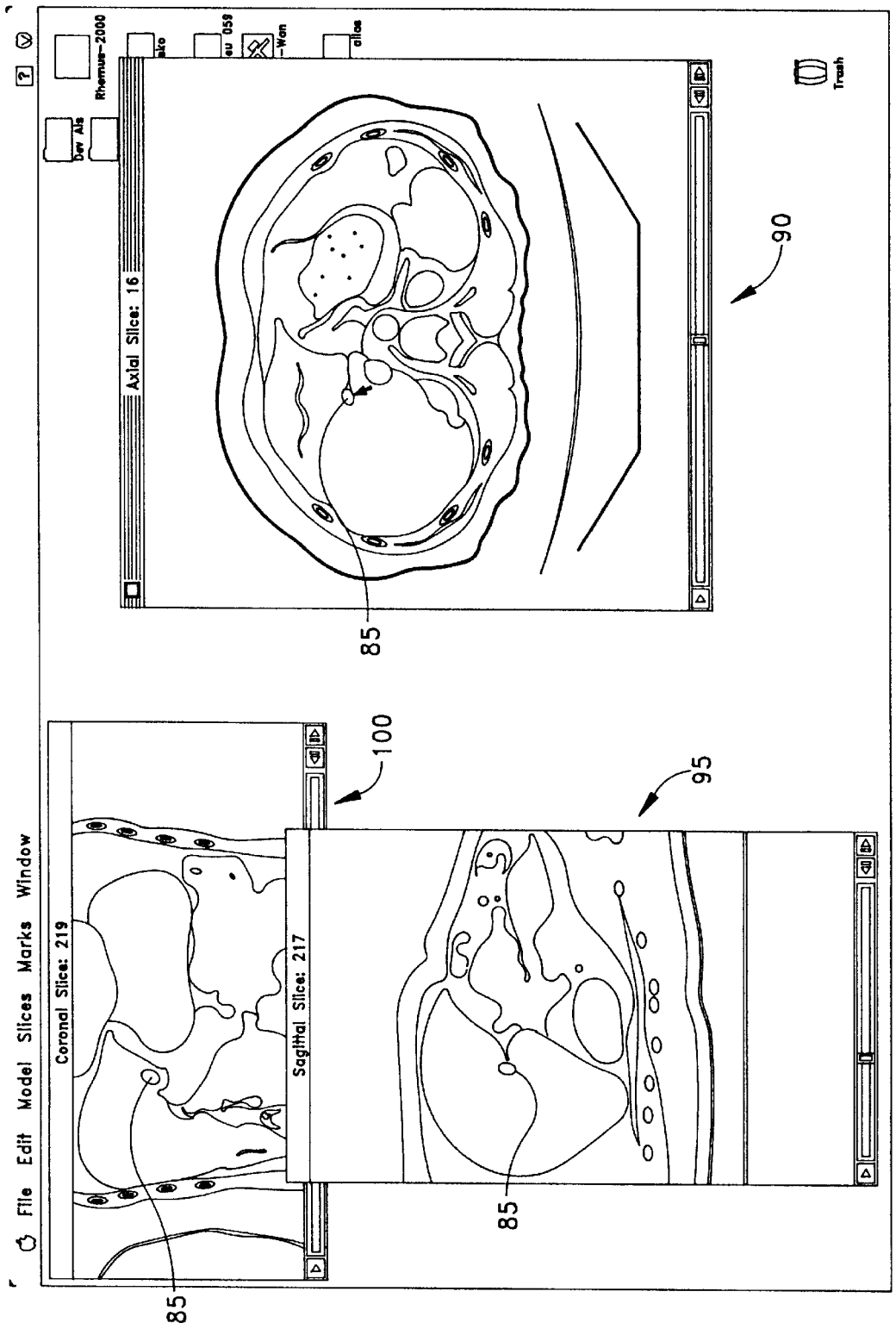
FIG. 14 illustrates three different 2-D slice images being displayed on a computer screen at the same time, with a marker being incorporated into each of the images.

In connection with the present invention, the sagittal and coronal 2-D slice image data may be stored with the axial slice image data in second section 40 of data storage device or medium 30. Preferably these sagittal and coronal slice images are stored in exactly the same data format as the 2-D axial slice images, whereby they may be easily accessed by computer 50 and displayed on display 60 in the same manner as has been previously discussed in connection with axial 2-D slice images. As a result, axial, sagittal and coronal 2-D slice images can be displayed on display 60, either individually or simultaneously in separate windows, in the manner shown in FIG. 14. Furthermore, when generating a composite image of the sort shown in FIG. 12 (i.e., an image generated from both the 3-D computer model contained in first section 35 of data storage device or medium 30 and a 2-D slice image contained in second section 40 of data storage device or medium 30), the composite image can be created using axial, sagittal or coronal 2-D slice images, as preferred.

It is also to be appreciated that the system of the present invention could be configured to generate and utilize oblique 2-D slice image date in place of the axial, sagittal and coronal slice image data described above.

In a further aspect of the present invention, it is possible to display a specific 2-D slice image in a window opened on display 60, place a marker into that specific 2-D slice image using a mouse or other input device 55, and then have that marker automatically incorporated into both (i) the 3-D computer model contained in first section 35 of data storage device or medium 30, and (ii) any appropriate 2-D slice image data contained in second section 40 of data storage device or medium 30. As a result, when images are thereafter generated from the 3-D computer model contained in first section 35 of data storage device or medium 30 and/or from the 2-D slice image data contained in second section 40 of data storage device or medium 30, these subsequent images will automatically display the marker where appropriate. See, for example, FIG. 14, which shows one such marker 85 displayed in its appropriate location in each of the three displayed 2-D slice images, i.e., in axial slice image 90, sagittal slice image 95, and coronal slice image 100. It is to be appreciated that it is also possible for a marker 85 to be displayed in an image generated from the 3-D computer model contained in first section 35 of data storage device or medium 30; see, for example, FIG. 15, which shows such a marker 85.

Figure 15:
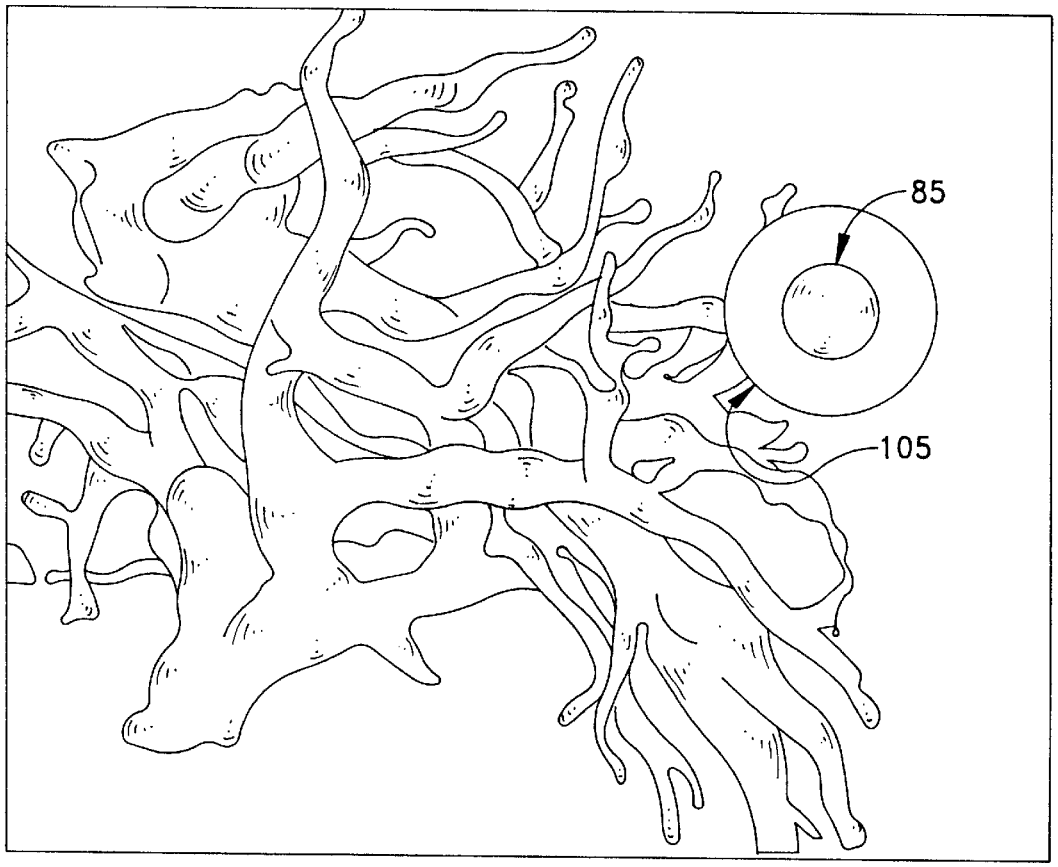
FIG. 15 illustrates a marker shown in an image generated from the 3-D computer model, with the marker being surrounded by a margin of pre-determined size.

In yet another aspect of the present invention, it is possible to generate a "margin" of some predetermined size around such a marker. Thus, for example, in FIG. 15, a margin 105 has been placed around marker 85. In this respect it is to be appreciated that margin 105 will appear as a 3-dimensional spherical shape around marker 85, just as marker 85 appears as a 3-dimensional shape, since the view of FIG. 15 is generated from the 3-D computer model contained in first section 35 of data storage device or medium 30. Alternatively, where marker 85 and margin 105 are displayed in the context of 2-D slice images, the marker and margin will appear as simple circles. Margin 105 can be used by a surgeon to determine certain spatial relationships in the context of the anatomical structure being displayed on the computer.

Figure 16:
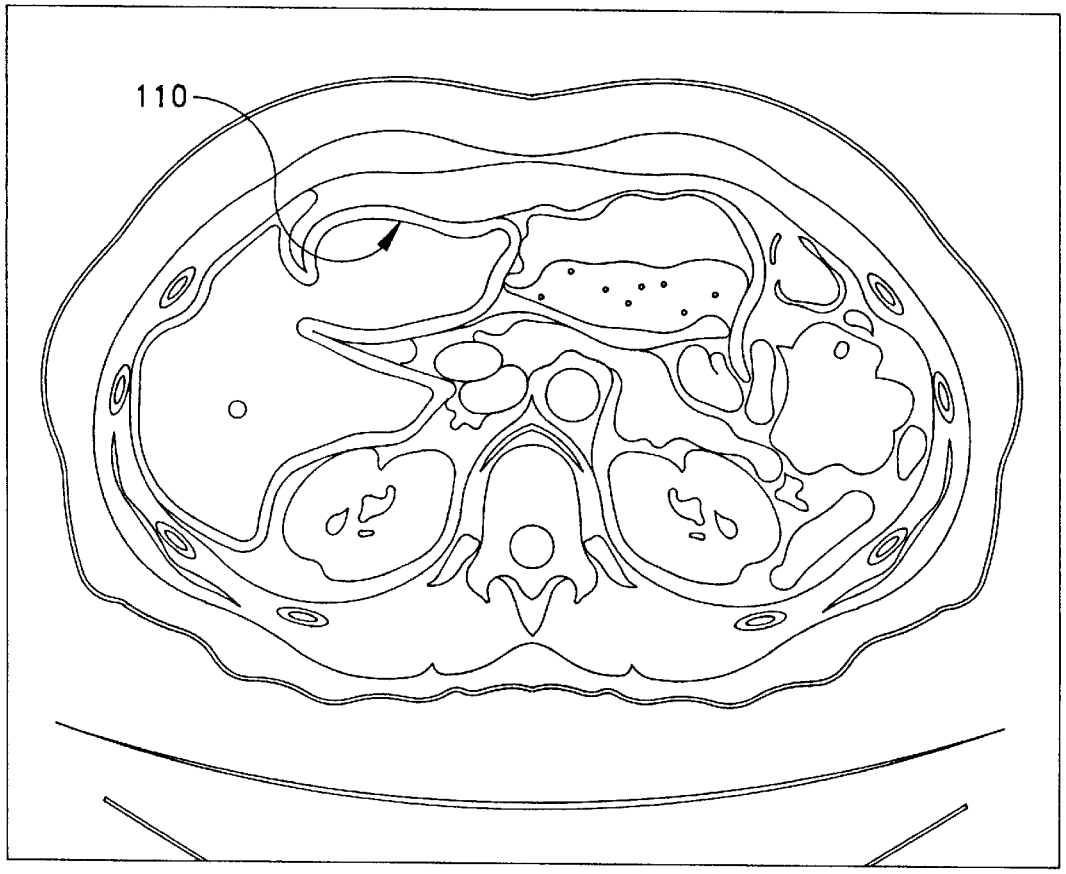
FIG. 16 illustrates a 2-D slice image, wherein the periphery of an object has been automatically highlighted by the system.

It is also to be appreciated that, inasmuch as the 3-D computer model contained in first section 35 of data storage device or medium 30 constitutes a plurality of software objects defined by polygonal surface models, it is possible to identify the periphery of any such objects in any corresponding 2-D slice image data contained in second section 40 of data storage device or medium 30. As a result, it is possible to highlight the periphery of any such object in any 2-D slice images displayed on display 60. Thus, for example, in FIG. 16, a boundary 110 is shown outlining the periphery of an object 115 displayed in a 2-D slice image.

Furthermore, while in the foregoing description the present invention has been described in the context of an anatomical visualization system, it is also to be appreciated that the system could be used in conjunction with inanimate objects, e.g., the system could be used to visualize substantially any object for which a 3-D computer model and a collection of 2-D slice image data can be assembled.

It is also anticipated that one might replace the polygonal surface model discussed above with some other type of surface model. Thus, as used herein, the term "surface model" is intended to include polygonal surface models, parametric surface models, such as B-spline surface models, quadralateral meshes, etc.

In yet another form of the present invention, the visualization system may incorporate means for determining patient-specific anatomical dimensions using appropriate scanned 2-D image data.

For purposes of illustration but not limitation, this aspect of the present invention will be discussed in the context of measuring a patient's vascular structure in the region of the aortic/iliac branching. By way of further example, such measurement might be conducted in the course of repairing an aortic aneurysm through installation of a vascular prosthesis.

Figure 17:
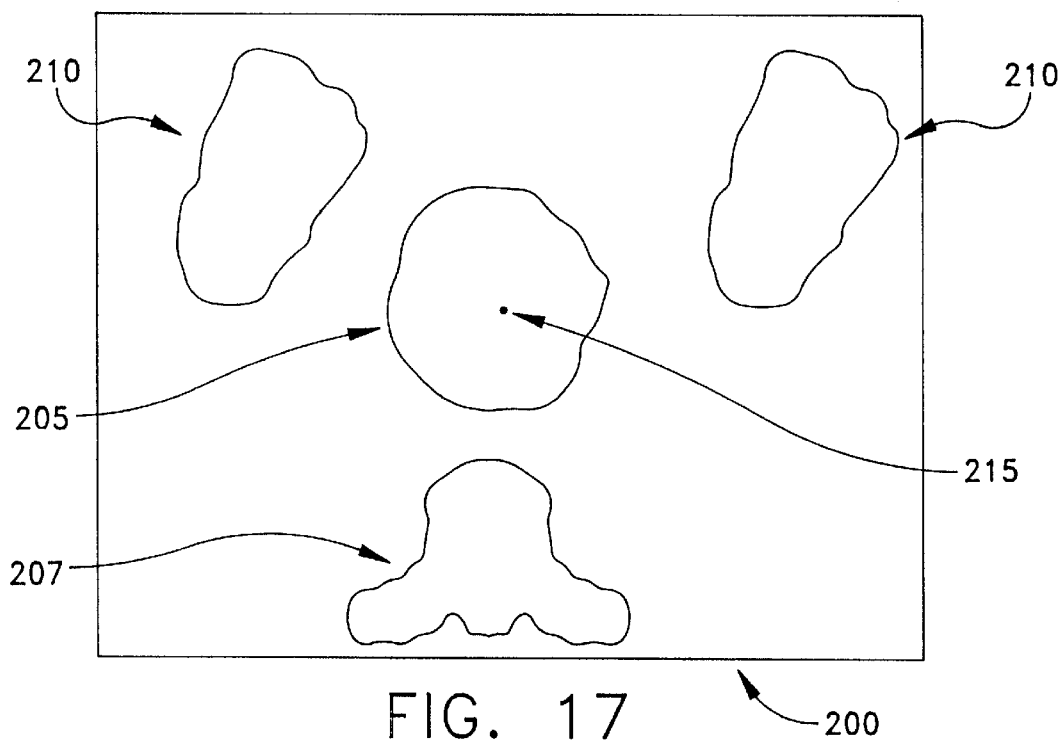
FIG. 17 is a schematic illustration showing various anatomical structures on a 2-D slice image, where that 2-D slice image has been taken axially through the abdomen of a patient, at a location above the aortic/iliac branching.
Figure 18:
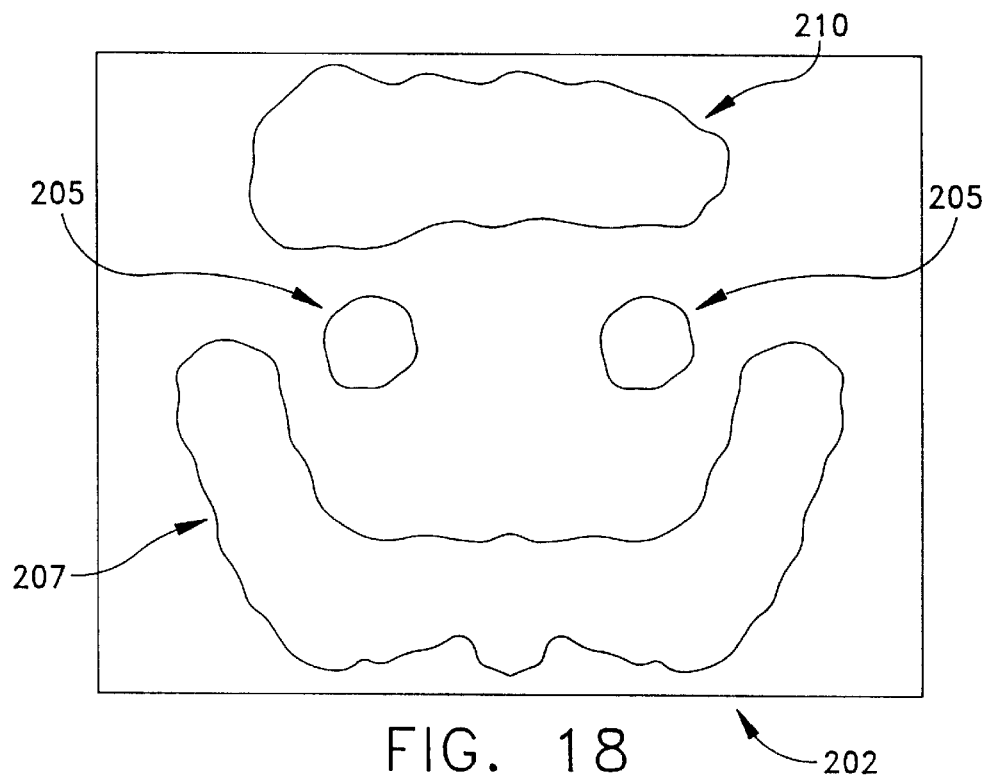
FIG. 18 is a schematic illustration showing various anatomical structures on another 2-D slice image, where that 2-D slice image has been taken through the abdomen of the same patient, at a location below the aortic/iliac branching.

More particularly, using the aforementioned scanning device 5, a set of 2-D slice images is first generated, where each 2-D slice image corresponds to a specific viewing plane or "slice" taken through the patient's body. As noted above, on these 2-D slice images, different types of tissue are represented by different image intensities. By way of example, FIG. 17 illustrates a 2-D slice image 200 taken through the abdomen of a patient, at a location above the aortic/iliac branching; FIG. 18 illustrates a 2-D slice image 202 taken through the abdomen of the same patient, at a location below the aortic/iliac branching. In these images, vascular tissue might be shown at 205, bone at 207, other tissue at 210, etc. An appropriate set of these 2-D slice images is assembled into a 3-D database so as to provide a volumetric data set corresponding to the anatomical structure of the patient. Referring back to the system illustrated in FIG. 6, the set of 2-D slice images making up this 3-D database might be stored in second section 40 of data storage device or medium 30.

Figure 17A:
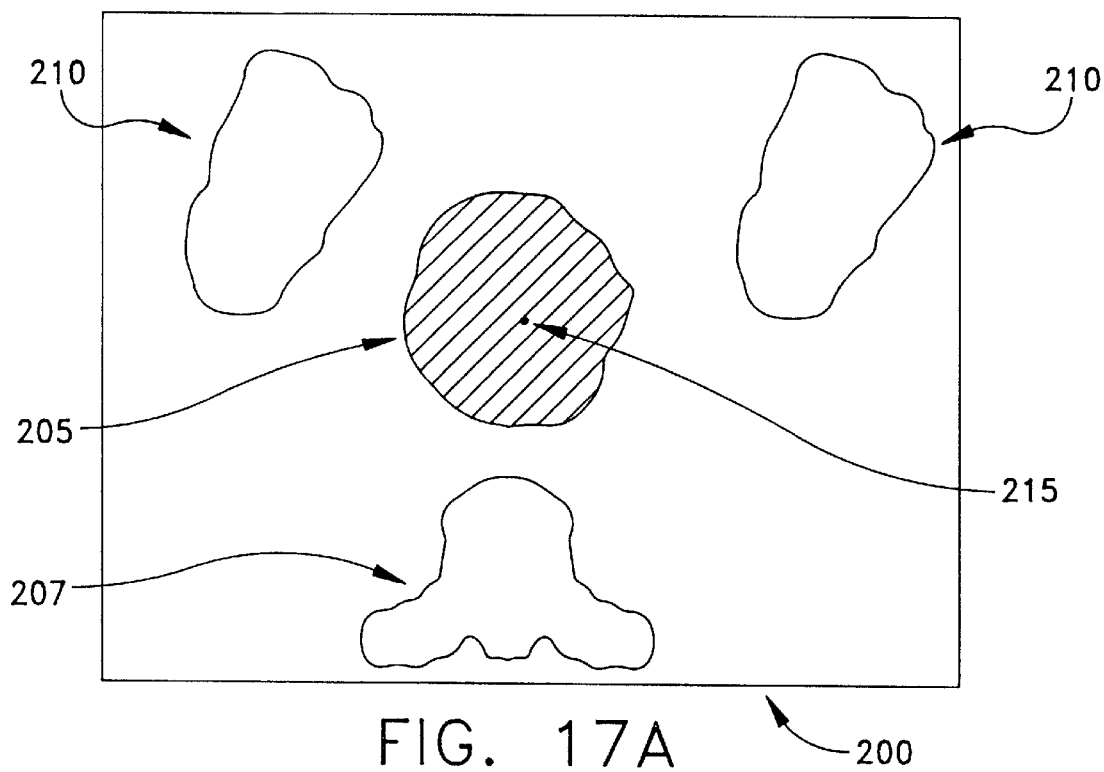
FIGS. 17A and 18A are schematic illustrations like FIGS. 17 and 18, respectively, except that segmentation has been performed in the 3-D database so as to highlight the patient's vascular structure.
Figure 18A:
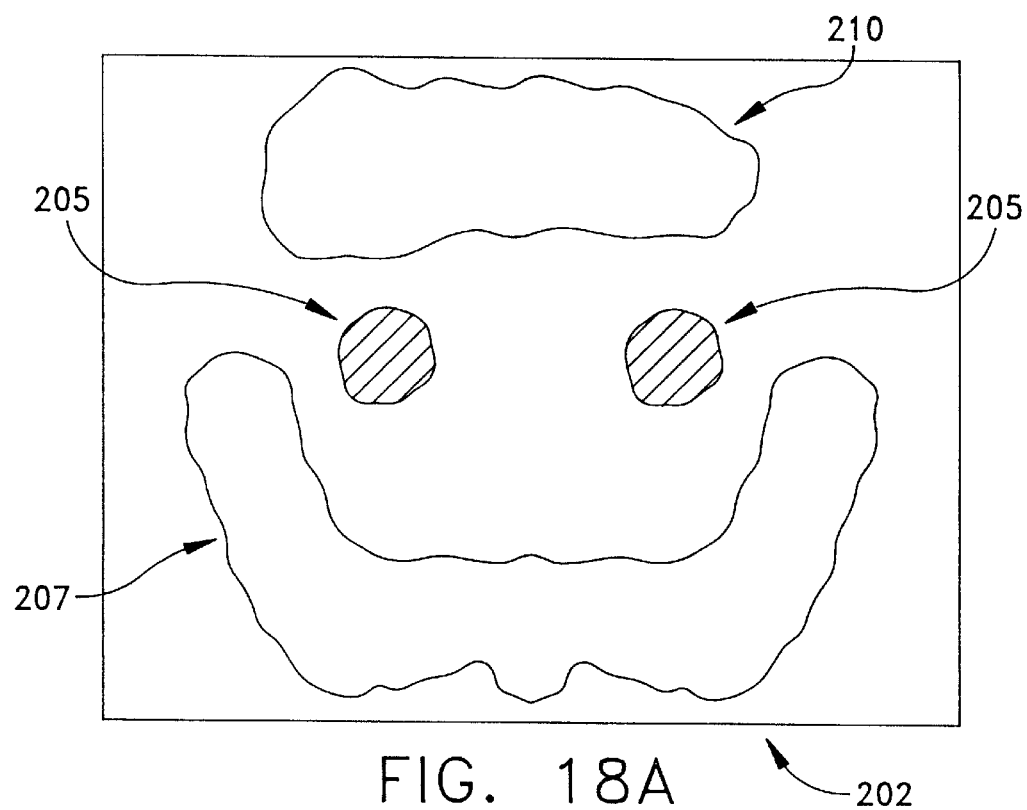

Next, using the appropriately programmed computer 50, the patient-specific volumetric data set (formed out of the collective 2-D slice images contained in the 3-D database) is segmented so as to highlight the anatomical structure of interest. This is preferably effected as follows. On the computer's display 60, the user is presented with 2-D slice images from the 3-D database, which images are preferably stored in second section 40 of data storage device or medium 30. As noted above, each of these 2-D images corresponds to a specific viewing plane or "slice" taken through the patient's body; or, stated slightly differently, each of these 2-D images essentially represents a plane cutting through the patient-specific volumetric data set contained in the 3-D database. As also discussed above, with each of these 2-D slice images, the different types of tissue will in general be represented by different image intensities. Using one or more of the input devices 55, e.g., a mouse, the user selects a particular 2-D slice image for viewing on display 60, e.g., "slice image #155". The user then uses one or more of the input devices 55 to select one or more points located within the anatomical structure of interest. For convenience, such user-selected points can be referred to as "seeds". See, for example, FIG. 17, where a seed point 215 has been selected within the interior of vascular tissue 205 so as to identify blood. The user also uses one or more of the input devices 55 to specify a range of image intensities that appear to correspond to the anatomical structure of interest in the volumetric data set, e.g., blood within the interior of a blood vessel. In accordance with the present invention, the appropriately programmed computer 50 then applies a segmentation algorithm of the sort well known in the art to segment out related structure within the patient-specific 3-D database. Preferably computer 50 is programmed to apply a 3-D connected component search through the volumetric data set contained in second section 40 of data storage device or medium 30 so as to determine the set of volumetric samples that are (i) within the range specified for blood, and which (ii) can be connected along a connected path back to one of the seeds where each of the locations along the path is also within the range specified for blood. The result of this 3-D connected component search is a set of 3-D locations in the volumetric data set which correspond to blood flowing through the blood vessel. For the purposes of the present illustration, this set of 3-D locations can be characterized as the "blood region". The segmented anatomical structure (i.e., the blood in the blood region) can then be highlighted on each of the 2-D slice images. See, for example, FIGS. 17A and 18A, where the segmented blood region in vascular tissue 205 has been cross-hatched to represent such highlighting.

Figure 19:
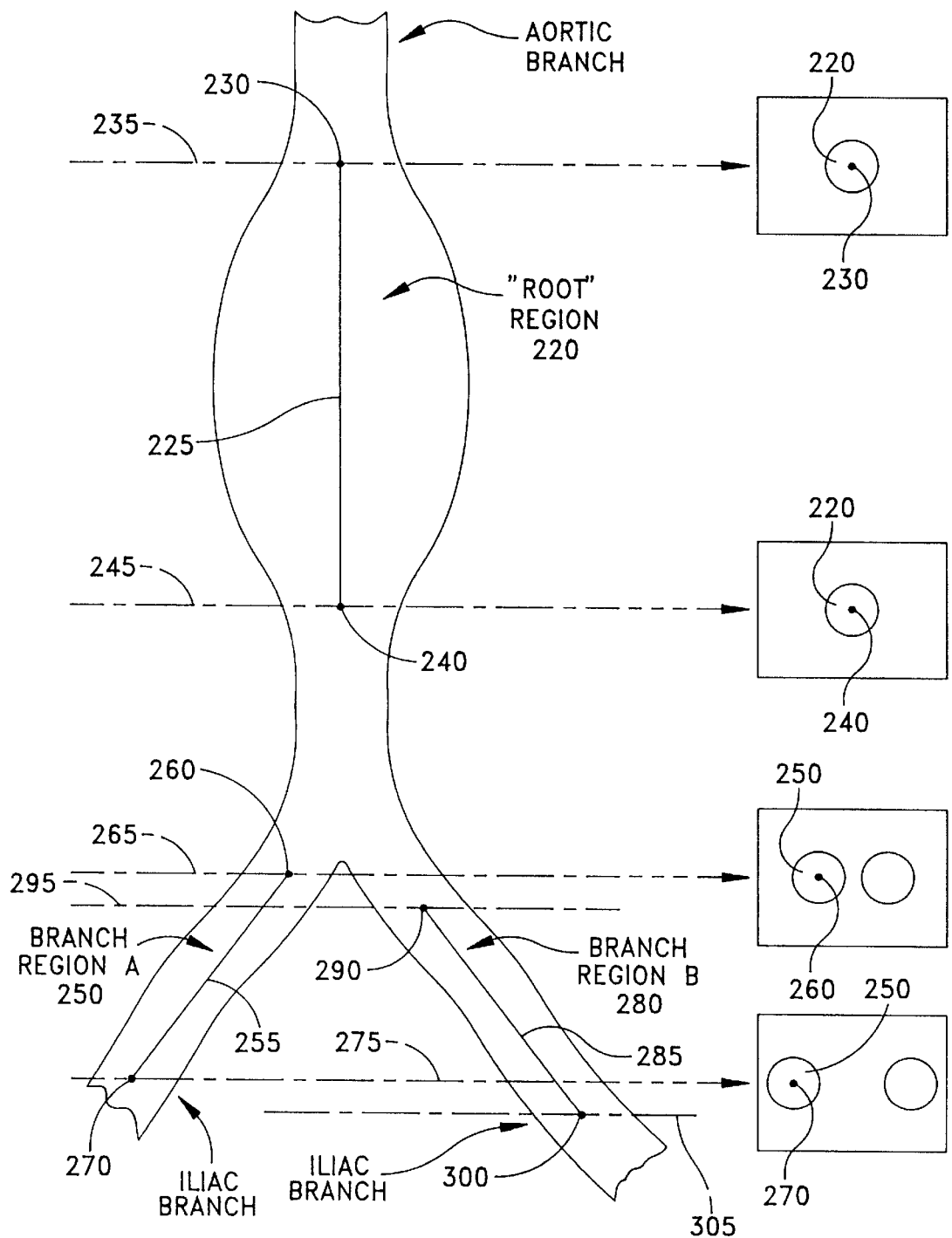
FIG. 19 is a schematic illustration showing that same patient's vascular structure in the region about the aortic/iliac branching, with branch lines having been specified for the patient's aorta and iliac branches.

Next, the branches in the segmented anatomical structure are identified. For example, and looking now at FIG. 19, in the present illustration dealing with vascular structure in the region of the aortic/iliac branching, the aortic and two iliac branches would be separately identified. This is done in the following manner. For each of the vessel segments that are part of the branching structure of interest, the user specifies a branch line in the volumetric data set that uniquely indicates that vessel segment. This is accomplished by using one or more of the input devices 55 to select, for each branch line, an appropriate "start" location on one of the 2-D slice images contained within second section 40 of data storage device or medium 30, and an appropriate "end" location on another one of the 2-D slice images contained within second section 40 of data storage device or medium 30. It should be appreciated that these branch lines do not need to cover the entire length of interest of the vessel and, in practice, will tend to stop somewhat short of the junction where various branches converge with one another. At the same time, however, for improved accuracy of modeling the branching structure, the branch lines should extend close to the branching point. For each of the vessel branches, the start and end locations are used to subdivide the blood region as follows: the region for that vessel branch is the set of locations within the blood region that are between the start plane and the end plane, where the start plane for each vessel branch is the 2-D image plane passing through the start location for the corresponding branch line, and the end plane for each vessel branch is the 2-D image plane passing through the end location for each vessel branch. Although the invention could be used for a more complex branching structure through obvious extensions, it is useful to consider a vessel branch structure consisting of just three vessel segments coming together at a branch point, e.g., a vessel branch structure such as the aortic/iliac branching shown in FIG. 19. In this case, the user would designate one vessel region as the root region (e.g., the aortic region 220 defined by a branch line 225 having a start location 230 contained in a start plane 235, and an end location 240 contained in an end plane 245) and the other vessel regions as branch region A (e.g., the iliac region 250 defined by a branch line 255 having a start location 260 contained in a start plane 265, and an end location 270 contained in an end plane 275), and branch region B (e.g., the iliac region 280 defined by a branch line 285 having a start location 290 contained in a start plane 295, and an end location 300 contained in an end plane 305), respectively.

Figure 20:
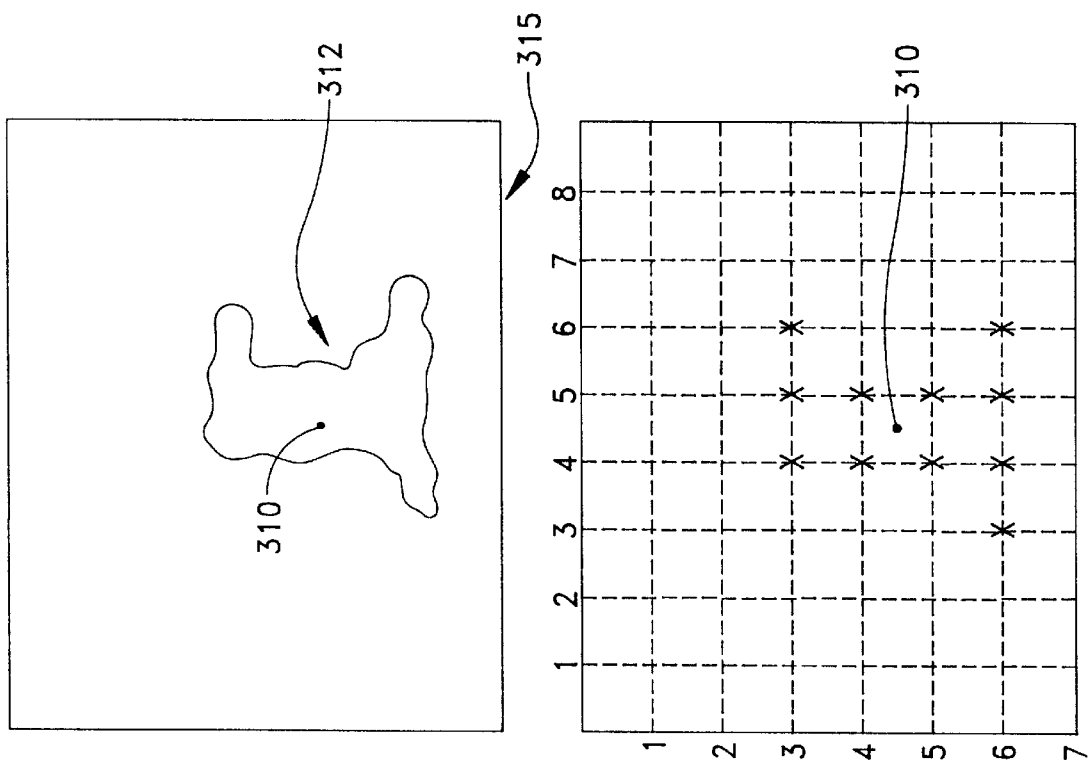
FIG. 20 is a schematic illustration showing how the centroid is calculated for the branch structure contained in a particular scanned 2-D image.
Figure 21:
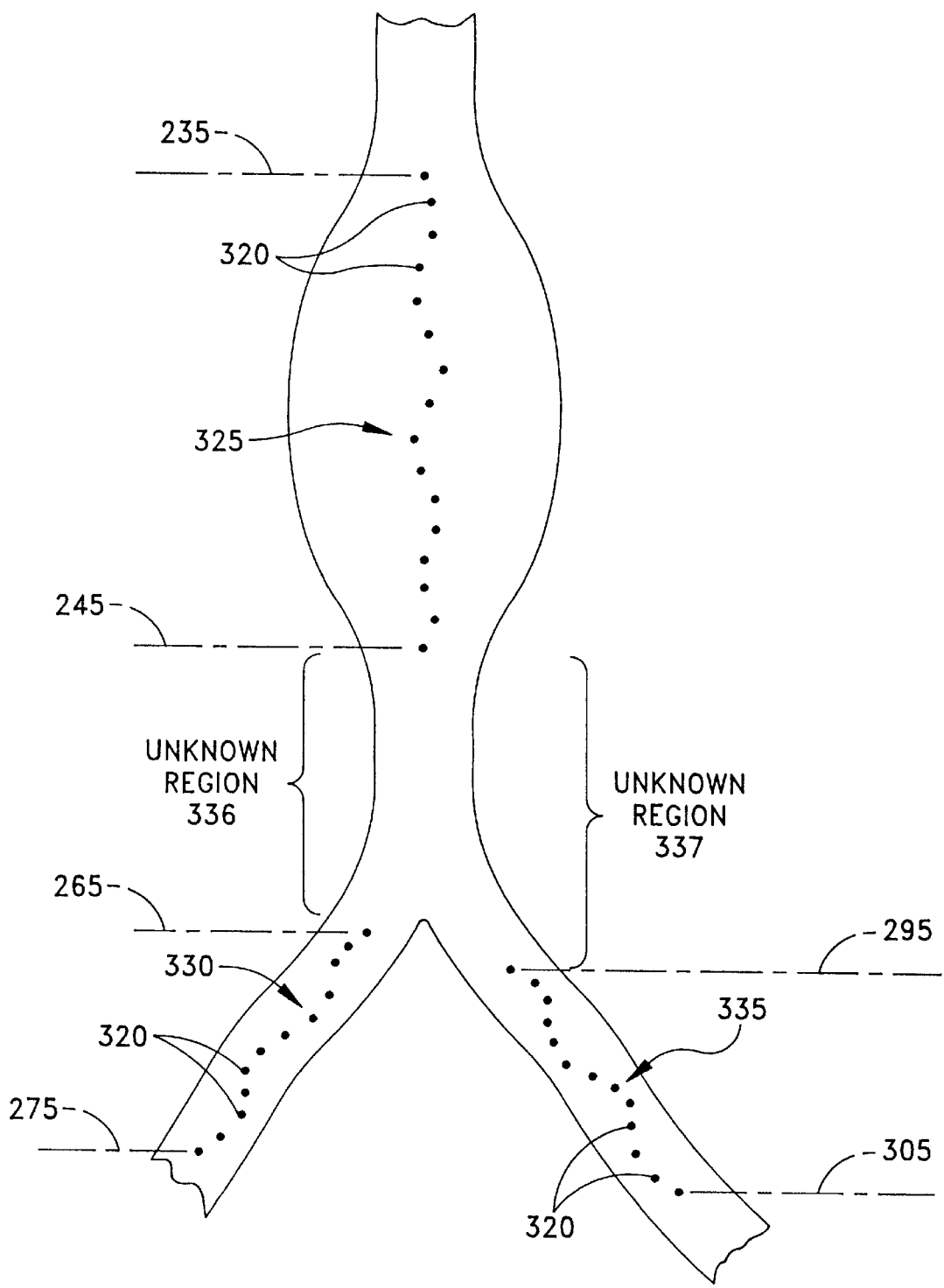
FIG. 21 is a schematic illustration showing the tortuous centroid path calculated for each of the respective branch lines shown in FIG. 19.

For each of the vessel regions determined in the previous step, a centroid path is then calculated. This is accomplished in the following manner. First, at intervals along the vessel line corresponding to the volumetric location of each of the original 2-D slice images contained in second section 40 of data storage device or medium 30, the centroid of the vessel region in that particular 2-D slice image is calculated. This is done by averaging the image coordinates of all locations in that 2-D slice image that are within the vessel region so as to yield a centroid point. See, for example, FIG. 20, which schematically illustrates the manner of calculation of the centroid 310 for a representative vessel region 312 in a representative 2-D image slice 315. The centroid path for each vessel region is then established by the collective set of centroid points located along that vessel segment in three-dimensional space. The tortuous path corresponding to the root region is called the root centroid path and the tortuous paths corresponding to branch regions A and B are called branch centroid path A and branch centroid path B, respectively. See, for example, FIG. 21, which shows a plurality of centroids 320, a root centroid path generally indicated at 325, a branch centroid path A generally indicated at 330, and a branch centroid path B generally indicated at 335, all shown in the context of a vessel branch structure such as the aortic/iliac branching example discussed above. It is to be appreciated that no centroids will be defined in the "unknown" region 336 bounded by the end plane 245 and the start plane 265, and the "unknown" region 337 bounded by the end plane 245 and the start plane 295.

Figure 22:
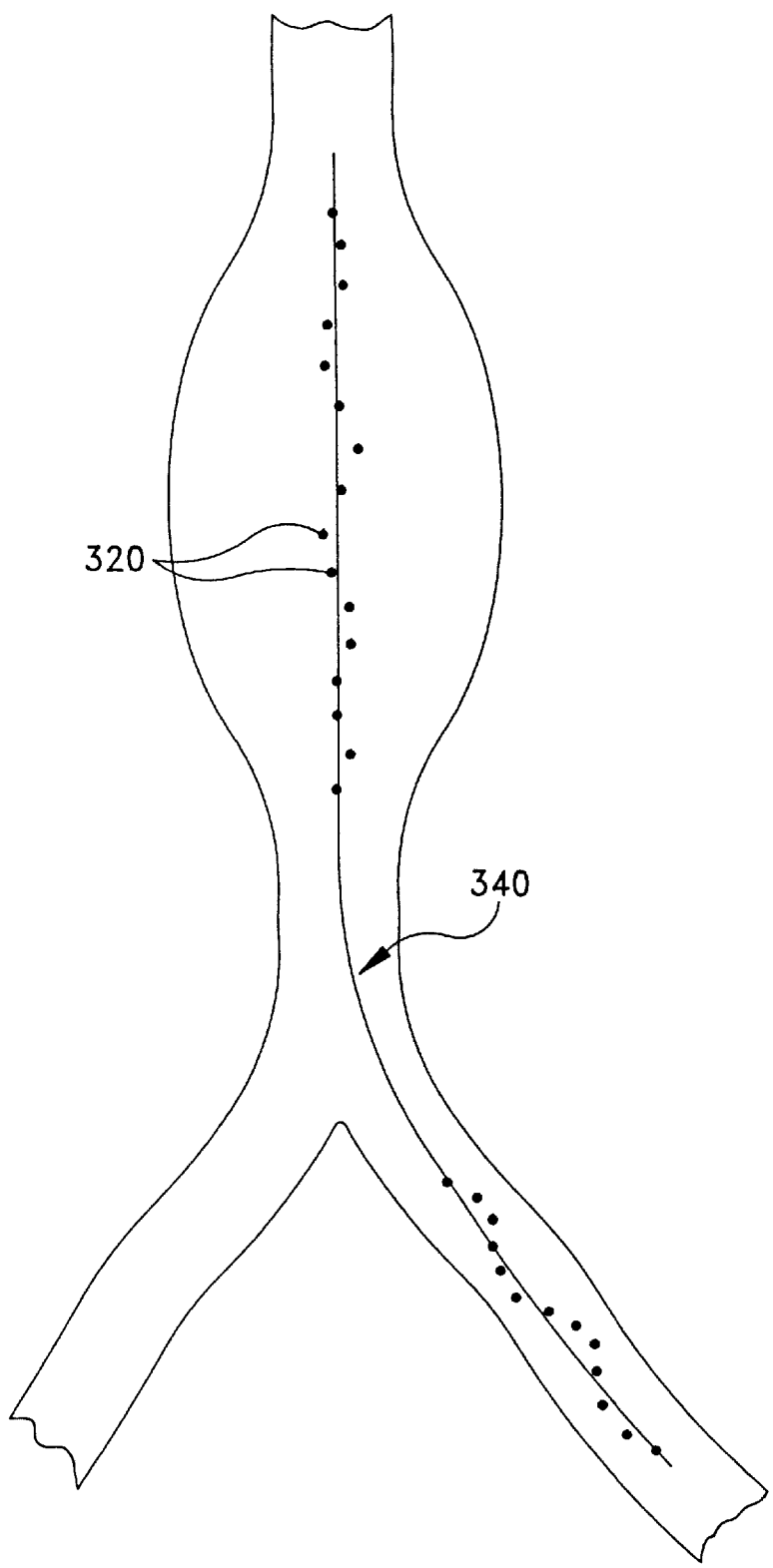
FIG. 22 is a schematic illustration showing the space curve determined by applying a curve-fitting algorithm to two of the centroid paths shown in FIG. 21, whereby the structure between the branch lines is filled out and the centroid data "smoothed" through a best fit interpolation technique.

The system then applies a curve-fitting algorithm to the tortuous centroid paths determined above so as to supply estimated data for any portions of the anatomical structure which may lie between the aforementioned branch lines, and for "smoothing out" any noise that may occur in the system. This is preferably done through a spline fitting algorithm effected in the following manner. First, two new paths are created, by concatenating the points in the root centroid path 325 with the points in each of the two branch centroid paths 330 and 335, so as to create a path root A and path root B. These two new paths are then used as the input to a B-spline fitting routine which selects the coefficients for a piecewise polynomial space curve that best approximates the points along the path in a least-squares sense. The number of pieces of the approximation and the order of polynomial may be varied by the user. The resulting curves may be called spline root A and spline root B. See, for example, FIG. 22, which illustrates the spline root B, generally indicated at 340.

Through numerical integration, the distance along the two splines (i.e., spline root A and spline root B) can then be calculated using standard, well-known techniques and the result can be presented to the user. These calculations can be used for a variety of purposes, e.g., to help determine the appropriate size of a vascular prosthesis to be used in repairing an aneurysm at the aortic/iliac junction. In addition, using well established mathematical techniques, at any point along the spline paths, a tangent vector and a perpendicular plane can be readily determined either by direct calculation or by definition in those cases where direct calculation would be undefined. By calculating the distance from the spline path to the points in the vessel branch region that are within an epsilon distance of the perpendicular plane, the shape of the vessel at that point can be determined, and the radius of a circle that best fits the cross-sectional area of the vessel at that point can also be readily calculated. Again, this result can be used to help determine that desired graft shape.

Figure 23:
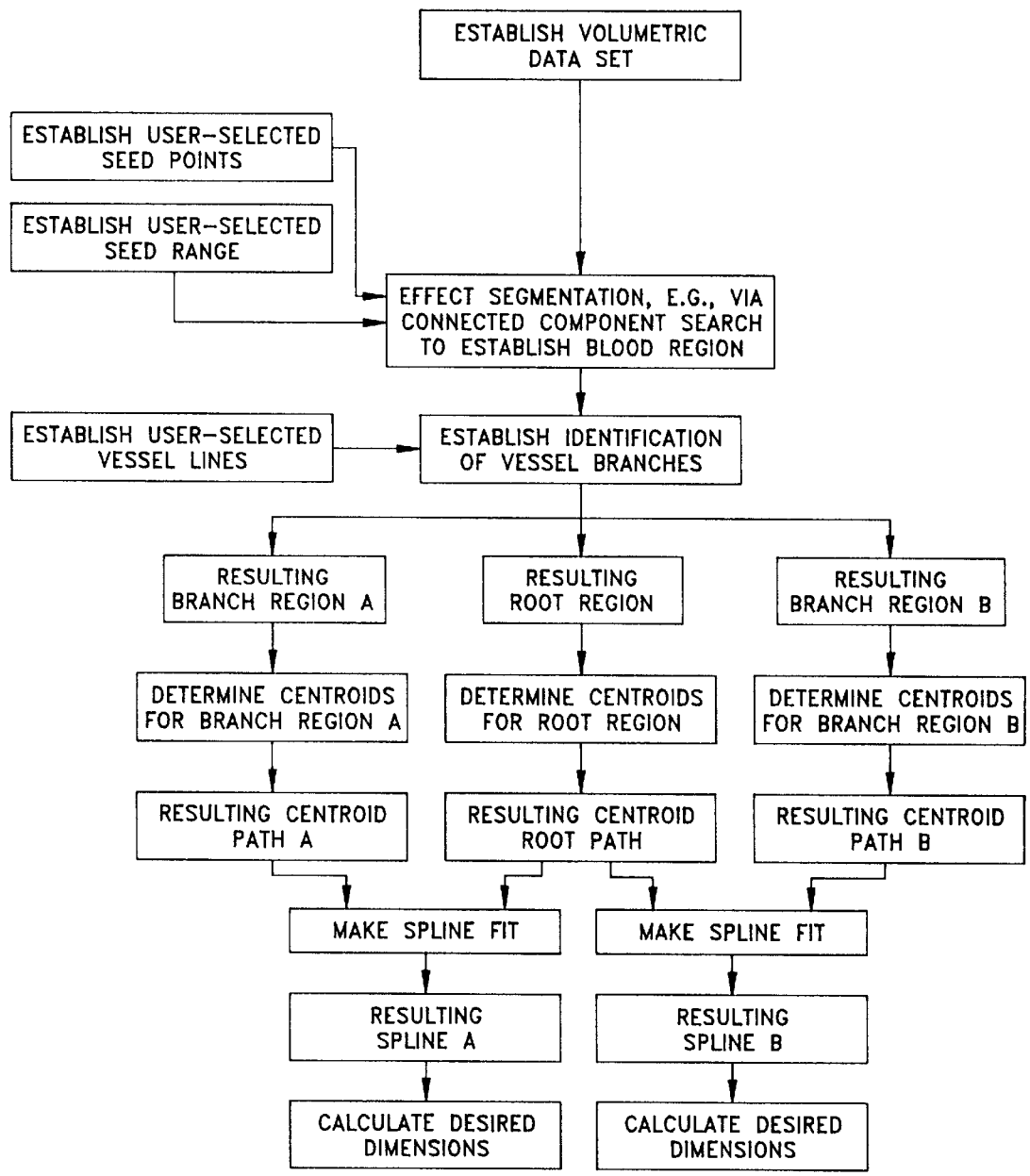
FIG. 23 is a flow chart illustrating how patient-specific anatomical dimensions can be determined from scanned 2-D image data in accordance with the present invention.

FIG. 23 is a flow chart illustrating how patient-specific anatomical dimensions can be determined from scanned 2-D data in accordance with the present invention.

It is also to be understood that the present invention is by no means limited to the particular construction herein disclosed and/or shown in the drawings, but also comprises any modifications or equivalents within the scope of the claims.

What is claimed is:

1. A system for determining patient-specific anatomical dimensions for structures which have a branching configuration using scanned 2-D image data, said system comprising:
    a set of scanned 2-D images assembled into a 3-D database, said 3-D database comprising a volumetric data set;
    means for segmenting said volumetric data set into a set of 3-D locations corresponding to a specific anatomical structure to be measured;
    means for defining a plurality of 2-D image planes parallel to and spaced from one another and transversely intersecting said set of 3-D locations corresponding to said specific anatomical structure, each of said 2-D image planes including a set of co-ordinates located within said anatomical structure to be measured;
    means for specifying, for each branching structure contained within said set of 3-D locations corresponding to said specific anatomical structure, a branch line in said volumetric data set that uniquely indicates said branch structure, said branch line being specified by a start location and an end location disposed in selected first and second ones of said plurality of 2-D image planes, respectively;
    means for calculating, for each branching structure contained within said set of 3-D locations corresponding to said specific anatomical structure, a centroid path in said volumetric data set for that branching structure, said centroid path being determined by averaging said set of co-ordinates located within each of said 2-D image planes between said first and said second ones of said plurality of image planes so as to define a centroid for the portion of said branch structure contained in that particular 2-D image plane, and applying a curve-fitting algorithm to said centroids so as to supply data for any portions of said set of 3-D locations corresponding to said specific anatomical structure which may lie between said 2-D image planes, and for smoothing out noise that may occur in said system, whereby to create resulting space curves; and,
    means for calculating said desired anatomical dimensions from said resulting space curves.

2. A system according to claim 1 wherein said segmenting means comprise means for conducting a connected component search.

3. A system according to claim 1 wherein said means for applying a curve-fitting algorithm comprise means for applying a spline-fitting routine.

4. A method for calculating patient-specific anatomical dimensions for structures which have a branching configuration by using 2-D image data, said method comprising the steps of:
    (A) assembling a set of scanned 2-D images into a 3-D database, said 3-D database comprising a volumetric data set;
    (B) segmenting said volumetric data set into a set of 3-D locations corresponding to a specific anatomical structure to be measured;
    (C) defining a plurality of 2-D image planes parallel to and spaced from one another and transversely intersecting said set of 3-D locations corresponding to said specific anatomical structure, each of said 2-D image planes including a set of co-ordinates located within said anatomical structure to be measured;

(D) specifying, for each branching structure contained within said set of 3-D locations corresponding to said specific anatomical structure, a branch line in said volumetric data set that uniquely indicates said branch structure, said branch line being specified by a start location and an end location on two of said set of scanned 2-D images disposed in selected first and second ones of said plurality of 2-D image planes, respectively;

(E) calculating, for each branching structure contained within said set of 3-D locations corresponding to said specific anatomical structure, a centroid path in said volumetric data set for that branching structure, said centroid path being determined by averaging said set of co-ordinates located within each of said 2-D image planes between said first and said second ones of said plurality of image planes so as to define a centroid for the portion of said branch structure contained in that particular 2-D image plane, and applying a curve-fitting algorithm to said centroids so as to supply data for any portions of said set of 3-D locations corresponding to said specific anatomical structure which may lie between said 2-D image planes, and for smoothing out noise that may occur in said system, whereby to create resulting space curves; and, (F) calculating said desired anatomical dimensions from said resulting space curves.

5. A method according to claim 4 wherein said segmenting is achieved by utilizing a connected component search.

6. A method according to claim 4 wherein said curve-fitting algorithm is a spline-fitting routine.

* * * * *